United States Patent [19]
Kulli

[11] Patent Number: 4,927,414
[45] Date of Patent: May 22, 1990

[54] SYRINGE WITH SAFETY RETRACTING NEEDLE

[76] Inventor: John C. Kulli, 1920 Spruce St., South Pasadena, Calif. 91030

[21] Appl. No.: 199,694

[22] Filed: May 27, 1988

Related U.S. Application Data

[63] Continuation-in-part of Ser. No. 43,691, Apr. 29, 1987, Pat. No. 4,747,831.

[51] Int. Cl.$^5$ .................................... A61M 5/24
[52] U.S. Cl. .................................... 604/110; 604/198
[58] Field of Search ............... 604/110, 195, 196, 197, 604/198, 192

[56] References Cited

U.S. PATENT DOCUMENTS

| | | | |
|---|---|---|---|
| 3,314,428 | 4/1967 | Johnson et al. | 604/192 |
| 4,507,117 | 3/1985 | Vining et al. | 604/196 |
| 4,692,156 | 9/1987 | Haller | 128/763 |
| 4,808,169 | 2/1989 | Haber et al. | 606/196 |

Primary Examiner—Stephen C. Pellegrino
Attorney, Agent, or Firm—Peter I. Lippman

[57] ABSTRACT

A hollow needle projects from the "forward" end of a syringe barrel or an adjacent auxiliary retraction barrel. After use to inject or withdraw liquid from a patient, the needle is released from the end of the barrel and retracted into the barrel. The barrel has an aperture big enough for the needle but too small for fingertips. The needle rides in a carrier block that slides in the barrel. Initially a manually releasable latch secures the block in the barrel against the forward end, with the sharp end of the needle protruding out through the aperture. The latch includes mutually interfering stop elements on the exterior of the block and interior of the barrel. After the injection or withdrawal of liquid, the person using the device withdraws the needle from the patient and manually triggers the latch by manipulating the plunger. A coiled spring drives the block rearward to retract the needle into the barrel. At the rear end of the barrel a stop halts the carrier block and needle to safely confine them. If no auxiliary barrel is present, the plunger is relieved to allow retention of the needle in the syringe, while the plunger is fully forward, to minimize bulk after retraction. In another form of the invention the front end of the plunger engages the rear end of the needle or carrier; pulling the plunger rearward pulls the needle into the syringe.

26 Claims, 9 Drawing Sheets

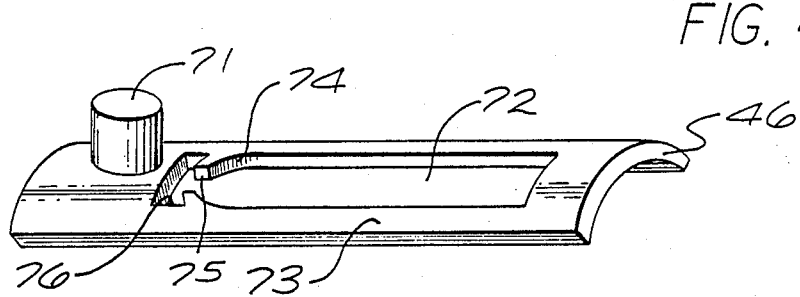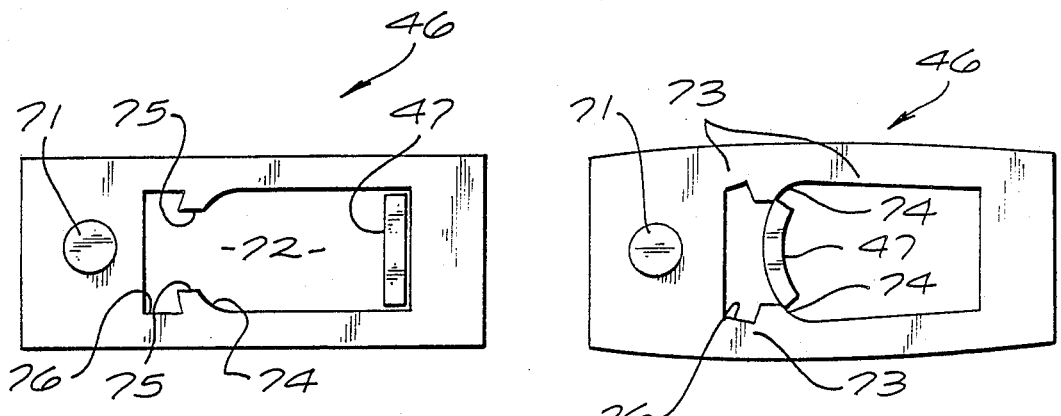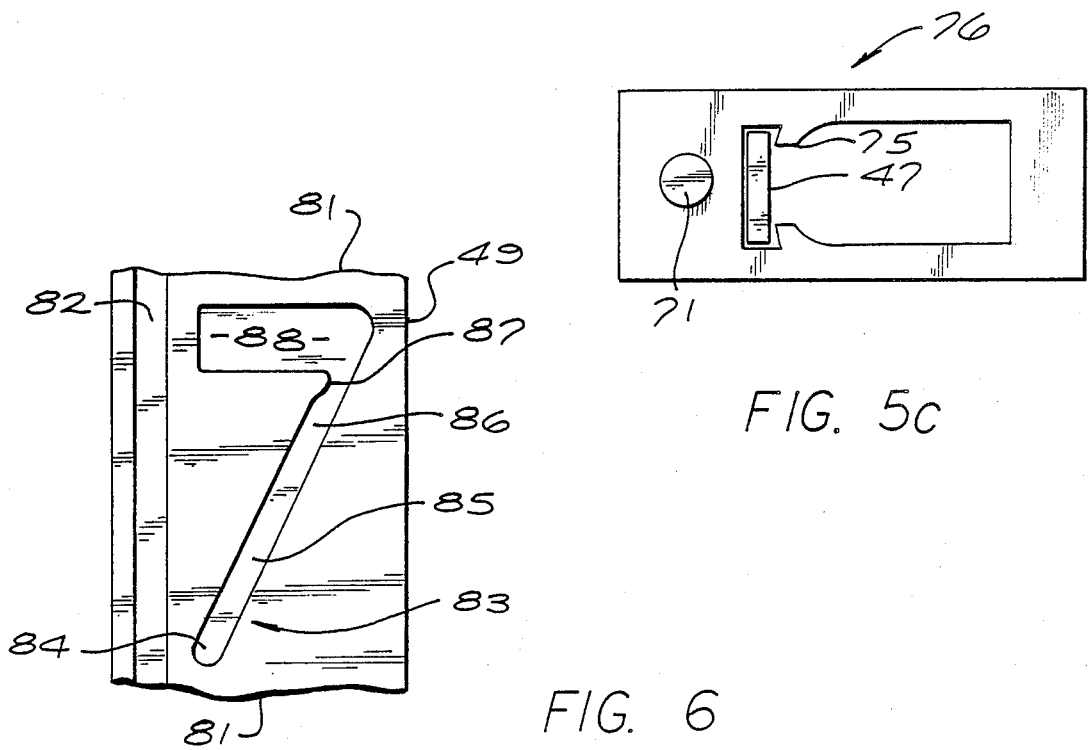

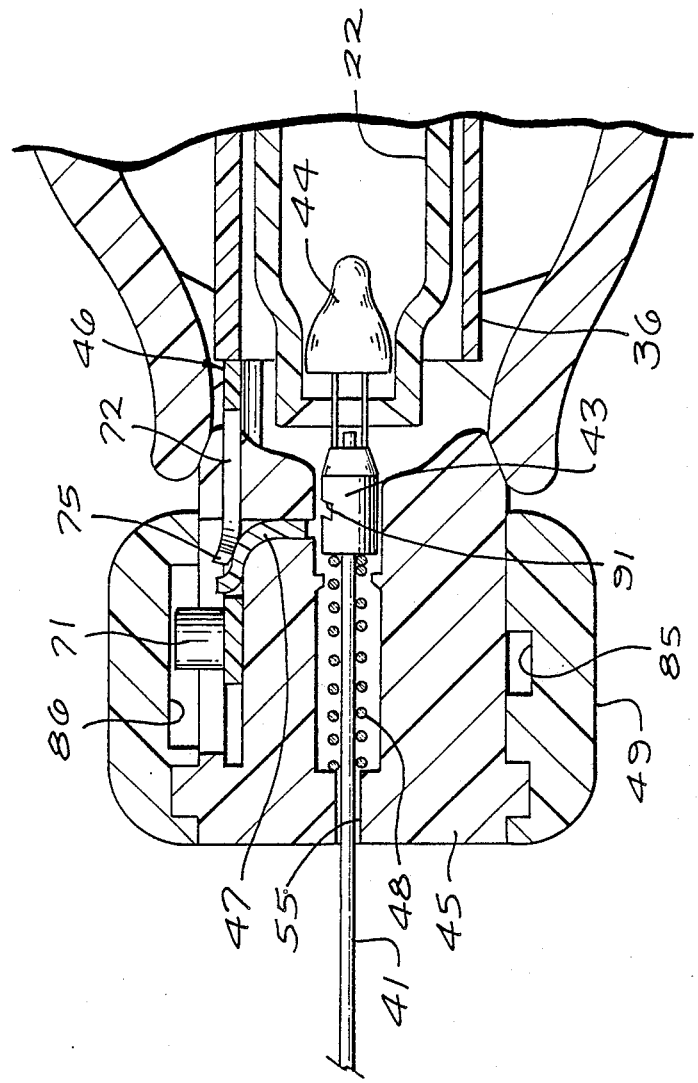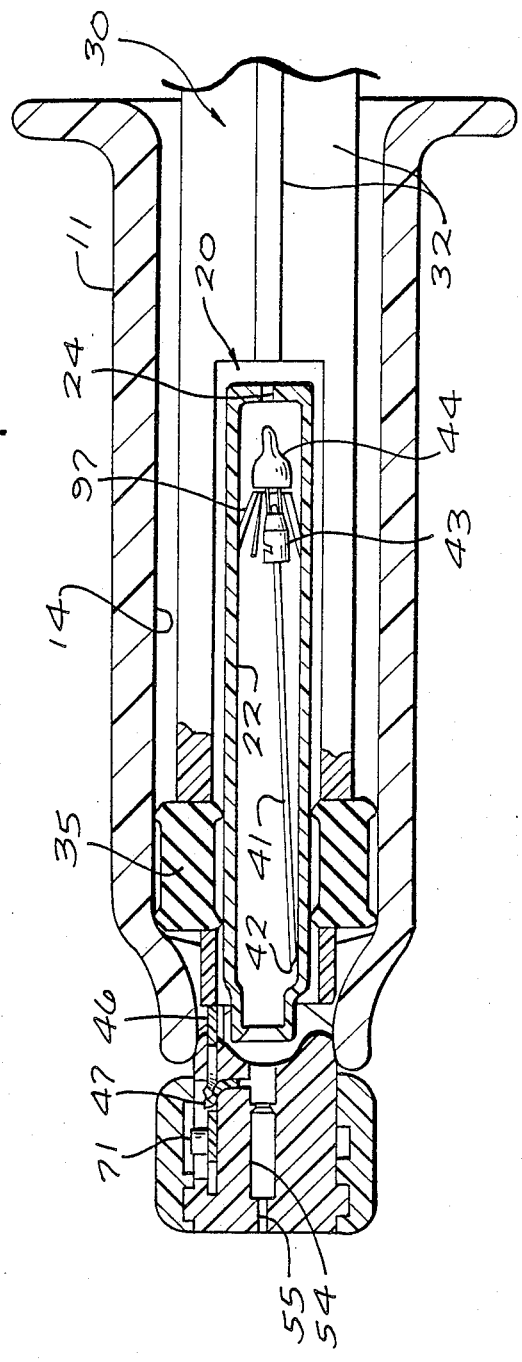

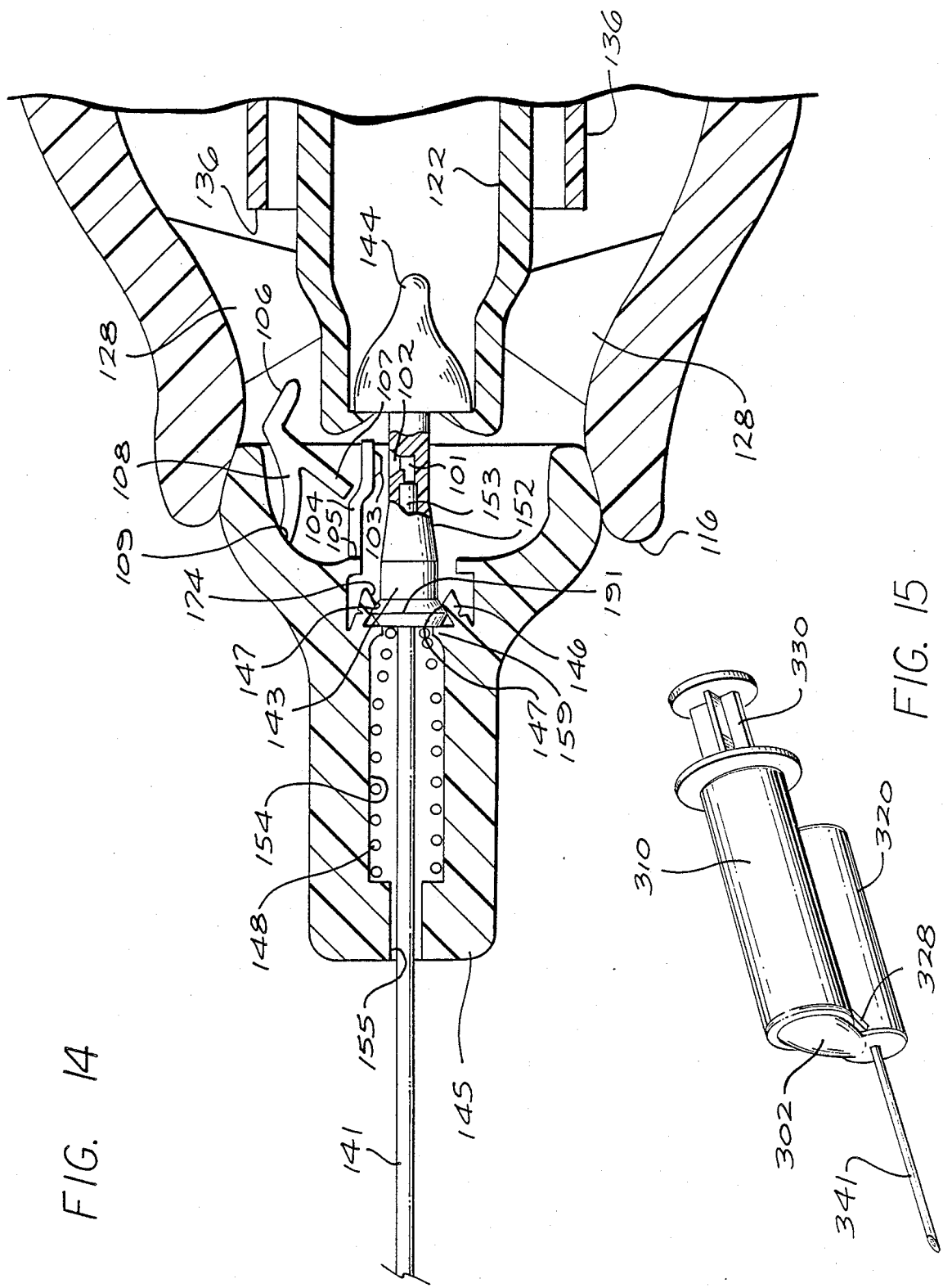

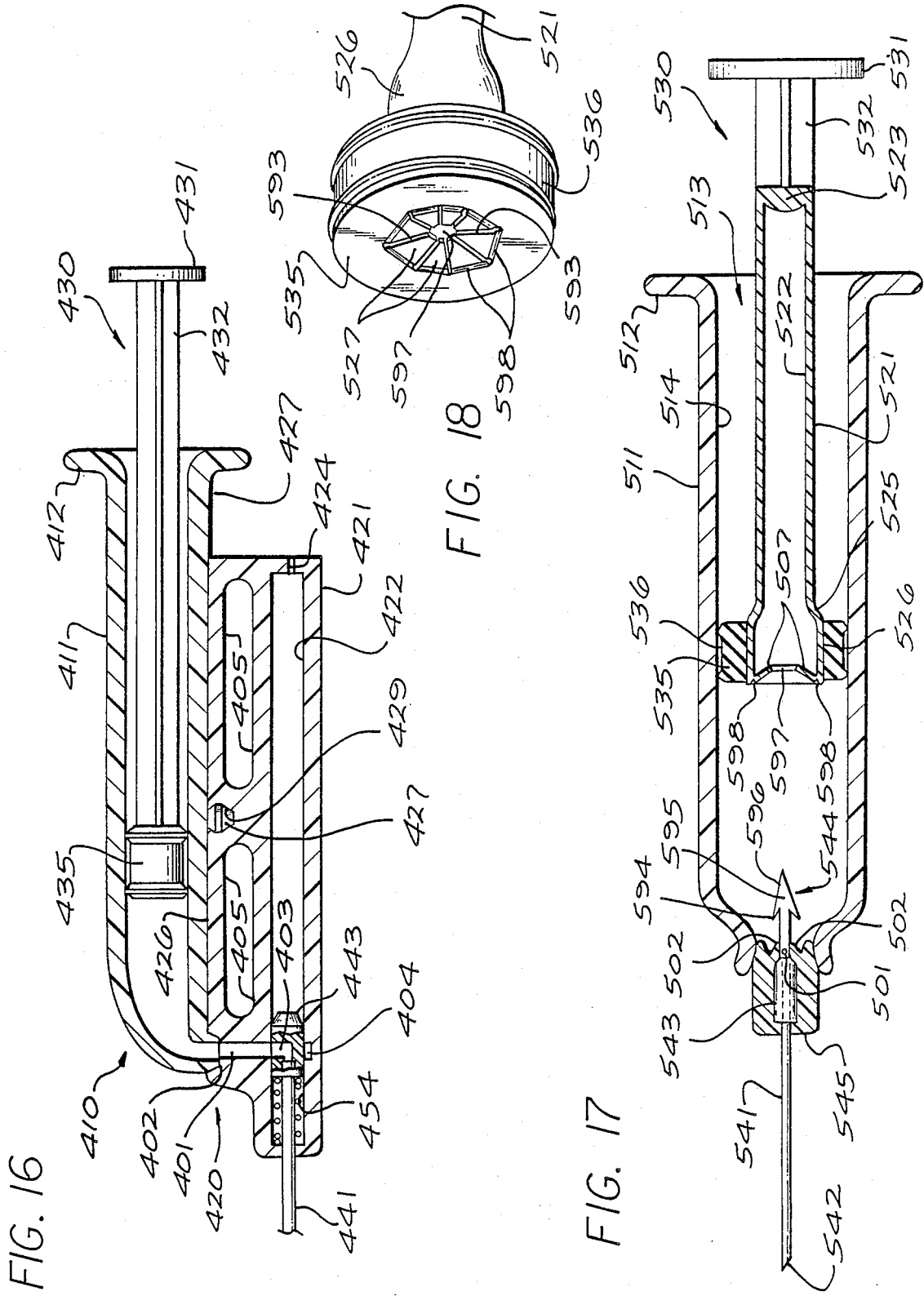

SYRINGE WITH SAFETY RETRACTING NEEDLE

RELATED APPLICATION

This is a continuation-in-part of U.S. Pat. Application 7/043,691, filed Apr. 29, 1987, and issued on May 31, 1988, as U.S. Pat. No. 4,747,831.

BACKGROUND

1. Field of the Invention

This invention relates generally to medical appliances; and more particularly to a special syringe for injecting liquids into or withdrawing liquids from a patient's body.

2. Prior Art

As is well known, there are myriad very important medical uses for syringes. It is also known in the medical community that a severe problem has developed in relation to all such devices.

That problem arises from the continuing presence of horrible diseases, particularly fatal and currently incurable diseases such as acquired immune deficiency syndrome ("AIDS") and hepatitis, transmitted by exchange of body substances between people. These diseases have led medical institutions to exclusively use disposable syringe needles for both injection and withdrawal of liquids from patients.

A severe residual risk remains, however, for medical personnel themselves in the inadvertent touching of needle tips after withdrawal from infected patients. Medical needles are designed and manufactured specifically to be extremely sharp and to puncture skin and flesh with only the slightest pressure.

As a result, what would ordinarily be an inconsequential scratch or pinprick can bring and has brought severe disease or even death to many medical staff members and others. Needless to say, health-care professionals are well aware of this risk and take considerable precautions to avoid such inadvertent punctures; thus the risk is reduced on a "probability" basis to an exceedingly small value.

Nevertheless, the exposure is so massive for working doctors, nurses and technicians that occasional punctures are inevitable. As a practical matter, it is virtually impossible for such an individual to reduce the incidence of accidental puncture to less than, say, one every year or perhaps one every few years.

Of course, not every such puncture follows contamination of the needle by a patient carrying a transmissible fatal disease. Nevertheless, there are enough medical personnel and enough such patients that a significant number of medical staffers die—and of course a greater number become very sick—from these accidents.

In discussion of this problem, needles of the types used with syringes commonly come to prominence. Though the word "hypodermic" has somewhat passed out of current usage in the medical profession, I shall for purposes of definiteness and simplicity refer to needles used with syringes for giving injections as "hypodermic needles". Needles used in drawing blood will be called "phlebotomy needles". By this terminology I mean to clearly distinguish all such needles from needles that are used for cannula insertion, the specific subject matter of my previously mentioned issued patent.

As detailed in that patent, the actual manual manipulations involved in using hypodermic and phlebotomy needles—as compared with cannula-insertion needles—are relatively favorable to avoiding puncture accidents. For that reason my first concern was for improvement of cannula-insertion needles.

The dangers of infection with hypodermic and phlebotomy needles nevertheless remain very important, partly because they are used in such enormous quantity. As noted in my patent, I did not mean to imply that hypodermic and phlebotomy needles are safe. There is an important potential for inadvertent unsheathing and many other kinds of accidents.

For example, as mentioned in my patent there are learning situations and emergencies, and circumstances in which the usual manual manipulations are complicated by patient mental or physical condition. While these situations are only a fraction of all instances of use of hypodermic and phlebotomy needles, this fraction nonetheless represents an enormous number of individual occurrences.

In a present-day standard, commercially available syringe, the needle is stainless steel, hollow, and extremely sharp at its frontal end. The shank of the needle is usually permanently fixed to a hub, which is screwed onto the frontal end of the syringe body so that the sharp end of the needle projects forward from the syringe body. The latter is a molded plastic cylinder, typically made of polycarbonate.

A plunger, or piston-and-handle combination, is fitted into the syringe body from the rear, and movably seals against the internal wall of the syringe body. In use, the plunger is first advanced fully.

Then, if the syringe is to be used for an injection, the needle is inserted into a supply of liquid to be injected; and the plunger is operated rearward to draw the liquid into the syringe body. The needle is then inserted into the patient and the plunger operated forward to expel the liquid into the patient.

If instead the syringe is to be used for withdrawal of liquid the needle is inserted into the patient's blood vessel—or in some cases into a body cavity abscess, or wherever fluid communication is to be established. The plunger is then operated rearward to withdraw blood or some other liquid from the patient as desired.

A separate safety cover is typically supplied in place on each needle. The separate safety cover firmly grips the needle hub and entirely covers the needle, to prevent accidental puncture and to prevent accidental contamination of the needle by substances in the environment, before use.

To use the needle, the safety cover must be entirely removed and set aside.

As already outlined, our focus of concern now shifts to the possibility that the needle may be contaminated by substances in the *patient, during* use. Accordingly the safety cover is to be replaced over the sharp end of the needle to prevent accidental puncture and, particularly, to prevent contact of people other than the patient, with possible contaminants on the needle.

It is here that the prior art fails to be effective, since the process of replacing the safety cover is subject to many risks of inadvertent mishandling as previously mentioned. The medical marketplace has seen various appliances and apparatuses aimed at solving this problem.

One such device is a special form of hypodermic needle, available commercially from the firm ICU Medical, Inc. under the trade name "ICU High Risk Needle". The ICU device is fitted with a sliding sheath that is carried on the shaft of the hypodermic needle itself.

After use the sheath is advanced forward over the needle tip.

That device undoubtedly serves a useful purpose, and it is certainly not my desire to criticize what is apparently the only commercial effort directed to an important problem. On the other hand, that device evidently has limitations that should be mentioned.

First, the ICU High Risk Needle is offered as a special item at a special price, for use only with patients known to be "high risk" patients. Not all patients carrying transmissible fatal diseases are known to be high risks.

Secondly, the sheath is attached halfway out the needle, where there would appear to be potential for inadvertent application of lateral force with sufficient leverage to snap off the needle. If that should occur before the sheath were fully advanced, the potential for accidental puncture could be substantial.

Thirdly, it is not clear from commercial literature on the product that the sheath locks in place when advanced—or, if so, that it locks firmly enough to withstand normal jarring in the workplace. Without such a feature, the device would seem to offer very limited protection.

A number of patents have been issued for devices that shield medical needles. Among these is U.S. Pat. No. 4,592,744, issued June 3, 1986, to Janine C. Jagger et al. This patent illustrates and describes a device that facilitates retraction of a hypodermic needle into a personnel-protective enclosure—which also serves as a handle for the device. The Jagger patent also shows and describes another device that similarly facilitates retraction of a phlebotomy needle into a like enclosure. In both of these devices the retraction procedure is relatively cumbersome.

In the hypodermic device, the needle is mounted by a relatively tight press fit to the forward end of a syringe that is fitted within the handle. The needle also extends in a relatively loose press fit through a hole in the front of the handle.

After use, the entire syringe must be pulled bodily out of the back end of the handle, carrying the needle rearward out of its front-end press fit with the handle, and into the cavity within the handle. The needle is carried in a flange that is too wide to escape from the rear end of the handle, and accordingly is pulled away from its tight press fit to the front end of the syringe.

The needle is thus trapped within the handle. The user must then dispose of the handle (with enclosed needle) and syringe separately.

In the Jagger phlebotomy device, the blood-collection receptacle is initially enclosed within an outer housing/handle during use. The sharp rear end of the needle passes in a tight friction fit through an elastomeric stopper on the receptacle.

Thereafter the receptacle is used as a tool to unscrew the needle from the forward end of the handle. Then the receptacle stopper is pulled off the rear end of the needle, so that the receptacle with its blood sample can be removed from the handle. As the receptacle is withdrawn the needle is trapped by its flange in the handle.

Thus the two forms of the Jagger invention that are described require the user to pull the needle all the way back through the hole in the handle, until the needle is entirely within the handle cavity—and then either discard two different bulky pieces or engage in a compound motion to reconfigure the appliance before disposal.

The large-amplitude motion required to pull the needle into the cavity is generally awkward and requires use of both hands. It may be considered acceptable, if not fully desirable. The disposal of two large pieces and the compound motion, however, are both more distinctly undesirable.

Even more undesirable, in both the hypodermic device and the phlebotomy device, are Jagger's arrangements for *arming* the apparatus for retraction of the needle. By "arming" I refer to a process of discriminating between (1) operation of the device, for drawing blood or loading a syringe before injection; and (2) retraction of the needle, for disposal.

Syringe operation includes filling the syringe, by pulling outward on the plunger, either in drawing blood or prior to an injection. Phlebotomy-device operation includes moving each vacuum vial outward after it is full.

Thus, in Jagger's syringe and phlebotomy device alike, operation necessarily involves rearward motion of some kind. Retraction of course also involves rearward motion.

The apparatus must somehow be made so that it will *not* retract the needle during such operation, but *will* retract the needle after operation. Jagger uses two different arming philosophies in her two different devices.

The two philosophies actually are opposite, and as a result have opposite drawbacks. Both sets of drawbacks, however, are severe.

I shall first consider the Jagger hypodermic needle. In that device, proper syringe operation and proper retraction thereafter both depend upon maintenance of the design relationships between two friction levels.

To fill the syringe a user must first advance the plunger fully forward, insert the needle tip into the patient's blood vessel or into a liquid to be injected, and then pull the plunger back. In pulling the plunger back, it would be extremely unnatural and awkward for the user to grasp the very short protruding rear end of the syringe; rather the user will grasp the outer handle or enclosure.

Thus the user relies upon relatively *high* friction between the needle-carrying nosepiece and the front end of the handle to keep the assembly together during loading. After loading and emptying of the syringe are complete, however, the user relies upon relatively *low* friction between those same two parts to break the assembly down for needle retraction and disposal.

In essence, the device is supposed to be self-arming for retraction. The user does nothing to prepare for needle retraction after use, but rather depends upon the two friction levels to discriminate between loading and retraction.

The relationship between these two friction levels, however, is too easily upset. For example, they can be disturbed by temperature variations in storage, beyond the knowledge of the person using the device. They can also be disturbed by leakage of congealable or sticky substances such as blood or sucrose solution, through the large opening at the rear of the handle and into the exposed seams between the handle and the needle flange.

The necessary friction relationships can also be disturbed by imperfect insertion of the syringe tip into its mating receptacle at the rear of the needle flange. That procedure, which in many cases is performed by medical technicians on site, rather than the manufacturer's personnel, can at least in principle damage either of the friction-fitting surfaces involved.

In such circumstances the syringe can be extracted from the needle flange before the needle is retracted—leaving no proper means for retraction. Conversely, the syringe can become stuck in place in the handle, requiring relatively forceful efforts by personnel to separate the parts for needle retraction.

Besides being an annoyance, forcible separation may lead to accidental punctures, thereby defeating the purpose of the safety device. All of this is a natural result of Jagger's design, which attempts to avoid the necessity for a physical arming step on the part of the user.

Now I shall turn to the Jagger phlebotomy needle. Here an arming step is required, but the required step is unduly cumbersome.

A user must unscrew the flange of the phlebotomy needle—using the last vacuum vial as a driver—before pulling the flange and needle back into the handle. This arrangement for retraction is likely to be bothersome to busy medical personnel, and therefore even more adverse to reliable, safe operation.

In effect Jagger's patent illustrates two opposing philosophies for retraction arming. One may be said to represent an inadequate arming step, and the other an excessive arming step. Both, however, tend toward the same result—a relatively ineffective device.

Other prior patents describe devices for automatic or semiautomatic resheathing of hypodermic syringes.

U.S. Pat. No. 4,026,287 to Haller is among the better of these, since it at least provides for retraction of the used needle into a cavity in a unitary, sturdy structure. The Haller device, however, requires screwing the syringe plunger into the back of the needle flange after use, to destroy a frangible seal around the flange and then retract the needle.

Haller also fails to protect against inadvertent insertion of fingertips into the syringe barrel. Even more serious is the fact that Haller's syringe plunger can remain in place, held only by detents at the rear of the barrel.

The Haller plunger thus remains dangerously ready to drive the needle forward again if the syringe is accidentally jarred past the detents. In addition, Haller's device and most of the others discussed below are disadvantageous in that their after-use sheathing configurations are at least as long as—or in some cases longer than—the initial or before-use configurations.

A device to be discarded, particularly one that is dangerous if broken open, should not be so extended and should not have a multiple-stage structure. Such configurations invite breakage and potentially serious accident.

U.S. Pat. No. 4,631,057 to Mitchell also leaves the needle accessible to fingertips through the unsealed forward end of the sheath. Mitchell's device also shares with the Haller device an undesirable sensitivity to jarring the device out of its safety detents, and in addition a similar undesirable extended after-use configuration.

Other patented devices with a like vulnerability to jarring out of detents and a like extended postuse configuration, but at least providing better frontal shielding against fingertip insertion, are U.S. Pat. Nos. 4,573,976 (Sampson), 4,643,199 (Jennings, Jr. et al) and 4,643,200 (Jennings, Jr.).

Worthy of mention for its provision of more positive resistance to jarring of the needle out of retracted position is U.S. Pat. No. 4,425,120 to Sampson et al. That device pays for its better safety locking with complexity of the manual manipulations required in use.

Similar observations apply to U.S. Pat. No. 3,890,971 to Leeson, which offers a relatively very compact and stable postuse configuration, but at the cost of a relatively complicated mechanism and large-amplitude motions to effect the resheathing.

Numerous devices for providing merely visual shielding or screening of hypodermic syringes have also been patented. Among these are U.S. Pat. Nos. 2,876,770 (White), 2,674,246 (Bower) and 3,134,380 (Armao). Such devices are actually counterproductive with respect to present purposes, since they effectively conceal the presence of a dangerously sharp and possibly contaminated needle.

Thus the prior art has failed to provide an optimum safety device for use under modern conditions in the field of the present invention. No prior-art device provides the necessary sure and easy operation that is essential to the effectiveness of such protection.

SUMMARY OF THE DISCLOSURE

My invention is a safety device for use in injecting a liquid into, or withdrawing liquid from, a patient. It also serves thereafter to protect medical personnel, trash-handling personnel, and any other people who may have casual contact with the device after its use. The device protects all such individuals from contact with those portions of the device that have been within the patient.

The device of my invention includes a hollow needle for piercing the patient, and for guiding and carrying a liquid into or out of the patient. The needle has a hollow shaft with at least one sharp end.

My invention also has a syringe, which includes a syringe barrel for containing a quantity of the liquid. The syringe also includes a plunger.

The plunger is disposed at least partially within the syringe barrel. It is adapted to be moved forward within the syringe barrel—to drive the liquid out of the syringe barrel and through the hollow shaft into the patient.

In addition, the invention includes some means for securing the shaft of the needle to either the syringe barrel itself or an auxiliary retraction barrel that is fixed adjacent to the syringe barrel. For purposes of generality in description, I shall refer to these means as the "securing means". The sharp end of the needle projects from the syringe barrel or auxiliary barrel, whichever is present.

My invention further includes some manually actuable means for releasing the securing means—and for retracting the sharp end of the needle into the barrel (again, whichever type of barrel is present). These means I shall, again for generality, call the "releasing and retracting means". Retraction of the needle by these means is substantially permanent.

The releasing and retracting means are manually actuable by a simple unitary motion. By "simple unitary" motion I mean a motion that is not compound, one that entails a single-stage stroke or movement in just one direction.

In a first group of preferred embodiments of my invention, the amplitude of this motion is substantially shorter than the length of the needle. Alternatively, it may be described as small compared with the size of the user's fingers, or hand generally.

In a second group of preferred embodiments of my invention, the amplitude of motion may be somewhat larger than the length of the needle, as the retraction is powered manually by withdrawal of the syringe plunger. In this second group of embodiments, however, provisions are made for limiting the overall after-retraction length of the assembly for disposal.

In one provision for limiting the assembly length, the plunger is hollow, and in the process of retraction the needle comes to rest within the plunger. In this form of the invention, after retraction the plunger therefore can be fully advanced once again to render the assembly compact for disposal.

In another provision for limiting the assembly length, all or part of the plunger itself separates from the barrel for separate disposal. This form of my invention is amenable to use with completely standard syringe needles.

(Some elements of these two main groups of embodiments are not mutually exclusive. In particular, for example, the short-amplitude-release embodiments may include a hollow plunger for needle storage after retraction.)

The foregoing may be a description of the preferred embodiments of my invention in their most general form. As will be appreciated, however, there are additional features which I prefer to incorporate in my invention to particularly optimize its efficacy. I shall mention some of those features here, reserving others for the detailed description that follows.

Such desirable and preferred features include a carrier structure that is fixed to and extending from the needle, and that forms a part of the securing means. The carrier structure is adapted to be restrained within the barrel to which the needle is to be secured, with the sharp end of the needle projecting from that barrel.

The carrier structure, when present, is also preferably responsive to the releasing and retracting means, to withdraw the needle into the barrel to which it is secured. It is also strongly preferable that a user be able to actuate these means without looking at the device during the actuation.

Preferably stop elements are respectively defined within the barrel and on the carrier structure. These elements engage each other to restrain the carrier structure from retracting the needle prematurely.

My invention preferably includes a trigger mechanism, forming part of the releasing and retracting means, that is operable from outside the barrel to which the needle is secured—and, in case that is the auxiliary retraction barrel, also outside the syringe barrel.

This trigger mechanism preferably includes a manually operable release member. When this member is operated, the trigger mechanism disengages the stop elements from one another to release the carrier structure and thereby retract the needle.

In addition I prefer to provide a manually operated arming system to lock out operation of the trigger until final phases of the syringe use are begun. This feature prevents inadvertent operation of the trigger, and in some forms of my invention is particularly helpful to facilitate filling of the syringe without initiating retraction.

Another preferred feature is an aperture, defined in the barrel to which the needle is secured, that is small compared with the fingers of such people to be protected—but large enough for passage of the needle.

Next, in this partial enumeration of desirable and preferred features, I shall mention some features that are particularly useful in the first group of embodiments—those involving short-amplitude actuating motion.

In these embodiments the releasing and retracting means preferably include some means, such as, for example, a coil spring, for positively biasing the sharp end of the needle toward retraction into the handle. These biasing means power the retraction.

As a result the releasing and retracting means are actuable by just one hand of a user of the device—a highly preferred mode of operation, since typical clinical situations require several necessary manual operations in a short time. Furthermore, after retraction has actually occurred, these biasing means preferably continue to operate, to *retain* the sharp end of the needle retracted within the handle.

Finally I shall mention some features that are useful in the above-mentioned second group of embodiments of my invention—in which the actuating motion is not necessarily of short amplitude. Generally in these embodiments the releasing and retracting means include mutually engaging means on a forward end of the plunger and on a rearward end of the securing means or needle.

By the action of these mutually engaging means, the needle is rearwardly retracted into the syringe by rearward manipulation of the plunger. In other words, the front of the plunger attaches to the rear of the needle or securing means, and the user pulls the plunger rearward to pull the needle into the syringe.

In these embodiments, although the plunger is not necessarily relieved, I prefer to relieve it so that the plunger can be again moved forward within the body to make the syringe assembly more compact for disposal. In this preferred arrangement the retracted needle is thus retained within the syringe—and in fact within the plunger, while the plunger is moved forward within the syringe body.

Alternatively, as mentioned earlier, after retraction the assembly may be shortened for disposal by removing all or part of the plunger. Since the piston portion of the plunger may have contacted the patient's blood, I prefer to make the apparatus so that the only portion of the plunger that separates from the barrel is the plunger shaft. In a syringe to be used exclusively for injection, however, the separable portion instead may be the entire plunger.

The foregoing operational principles and advantages of the present invention will be more fully appreciated upon consideration of the following detailed description, with reference to the appended drawings, of which:

BRIEF DESCRIPTION OF THE DRAWINGS

FIG. 4 is is a like perspective view of a retraction slide plate that is also part of the retraction mechanism of FIGS. 1 and 2.

FIGS. 5a through 5c are simplified plan views of the FIG. 4 slide plate and a carrier-structure retaining tongue that are also parts of the retraction mechanism, showing the interaction between the slide plate and retaining tongue during arming of the mechanism.

FIG. 6 is a diagram showing the cylindrical interior surface of an arming control ferrule as if unrolled to form a flat strip.

FIG. 12 is an enlarged longitudinal elevation similar to FIG. 2, and illustrating the same embodiment, but showing the device a fraction of a second after the release mechanism is actuated, with the needle moved very slightly back from its FIG. 4 position toward its retracted position.

FIG. 13 is a longitudinal elevation of the same embodiment, showing the needle fully retracted.

FIG. 14 is an enlarged longitudinal elevation similar to FIGS. 2 and 12, but illustrating another preferred embodiment in which retraction is triggered hydraulically.

FIG. 15 is a perspective view of a third preferred embodiment of my invention, in which the needle is secured to an auxiliary retraction barrel that is outside the syringe barrel. This view, like FIG. 1, shows the needle in extended position, before retraction.

FIG. 16 is a elevational view, mostly in longitudinal section, of a variant of the FIG. 15 embodiment in which the syringe section and the needle/retraction-barrel section are respective separate modules.

FIG. 17 is a like view of a fourth embodiment. In this embodiment the plunger is pulled back to retract the needle, and then advanced again to shorten the assembly for disposal.

FIG. 18 is an enlarged perspective view of the forward end of the plunger used in the FIG. 17 embodiment.

DETAILED DESCRIPTION OF THE PREFERRED EMBODIMENTS

Figure 1:
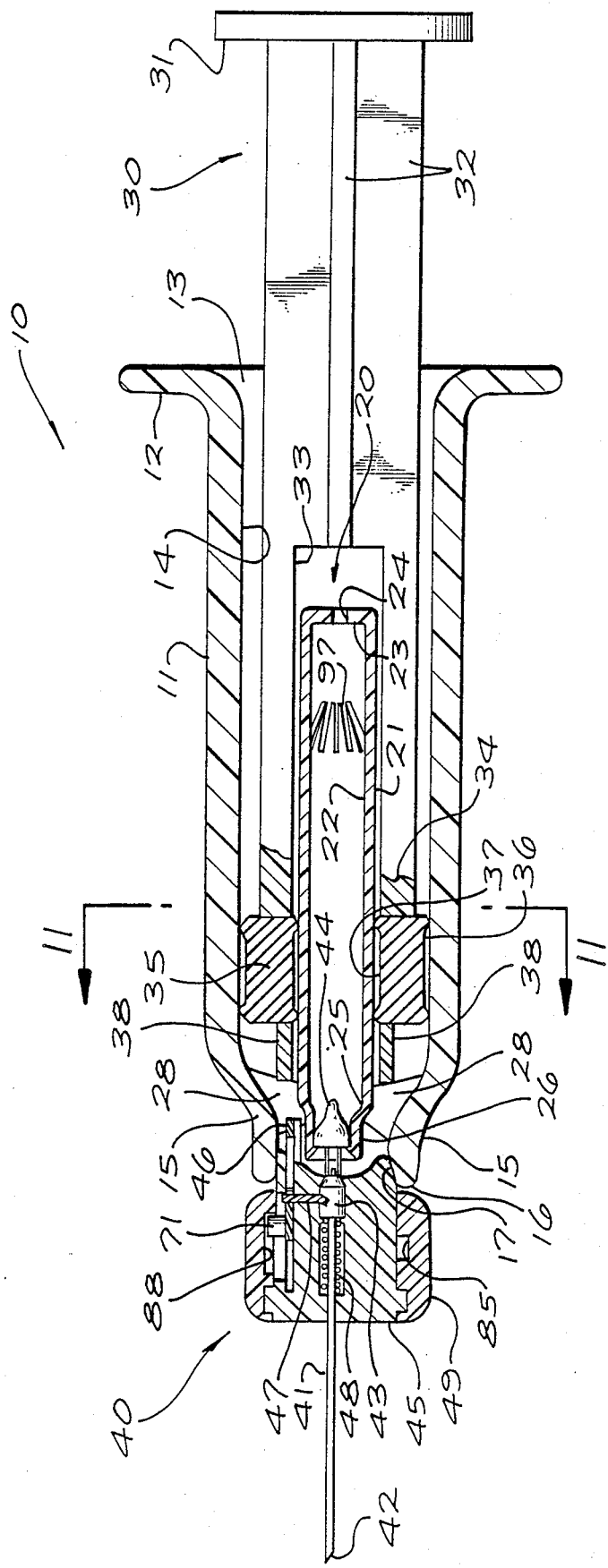
FIG. 1 is a side elevation, mostly in longitudinal section, of a preferred embodiment of my invention, shown with the needle secured in extended position directly to a syringe barrel—and before the releasing and retracting means are actuated to retract the needle into the barrel.

As shown in FIGS. 1 through 13, an embodiment of my invention which I now prefer includes a syringe barrel 10, an inner retraction barrel 20, a novel plunger 30, and a separate needle-and-hub assembly 40. Carried on the front end of the plunger 30 are an annular piston 35 and a forwardly extending retraction actuator boss 36. The needle-and-hub assembly 40 includes a needle 42 and a retraction mechanism 43 through 92.

The syringe barrel 10 has a generally cylindrical outer surface 11, expanding at the rear to a finger-grip external flange 12. To the rear of this flange 12 the barrel 10 has an open end 13 to admit the front end of the plunger 30, and the interior wall 14 of the barrel 10 is smooth and accurately cylindrical to seal movably against the periphery of the piston 35.

The front end of the barrel 10 tapers inward in a very generally frustoconical segment 15 to a narrower nose 16. The inside forward surface 17 of the nose 16 is also generally frustoconical, tapering outward very slightly to accommodate the complementarily shaped rear segment 51 of the hub in a tapered force fit. When so assembled, the needle-and-hub assembly 40 is tightly and accurately secured to the syringe nose 16.

Inside the tapered forward segment 15 of the syringe barrel 10 are four circumferentially spaced radial vanes 28 (only two being shown) that suspend the inner retraction barrel 20 coaxially within the outer cylinder 11. As will be seen, satisfactory operation of both the plunger and the retraction mechanism depends upon the accuracy with which the retraction barrel is coaxial—with the inner cylindrical wall 14 and the frustoconical force-fit surface 17, respectively.

The retraction barrel 20 has an accurately cylindrical outer surface to seal movably against the inner periphery of the annular piston 35, and a generally cylindrical inner chamber to receive the carrier structure 43, 44 and needle 42. Several rearward-faced retaining fingers 97 are formed near the rear end of the retraction barrel inside surface 22, to capture and retain the carrier structure 43, 44 after retraction. A small air-escape aperture 24 is formed at or near the rear end of the retraction barrel 20.

At the front end of the retraction barrel is a generally frustoconical portion 28, tapering forward to a narrower nose section 26 and inwardly projecting teeth or hooks 53. Some segments (not shown) of the outer wall of the narrower nose section 26 are relieved so that in those segments the wall is very thin and stretchable, and the teeth 53 can be forced outward slightly for passage of the rear part 44 of the carrier structure 43, 44.

Figure 9:
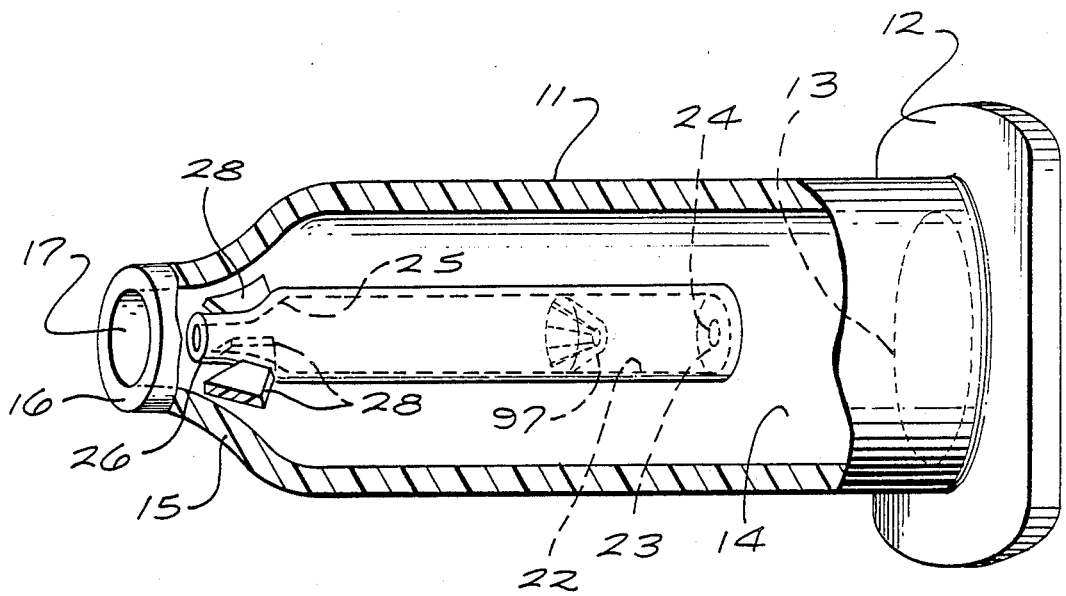
FIG. 9 is a general perspective view of a syringe barrel for use in the embodiment of FIGS. 1 through 8.

When the needle-and-hub assembly 40 is not in place, the nose section 26 of the retraction barrel collapses radially inward to form a closure as shown in FIG. 9. The forward surfaces of the teeth 53, however, taper outward toward the front for purposes to be explained below.

Figures 10, 11:
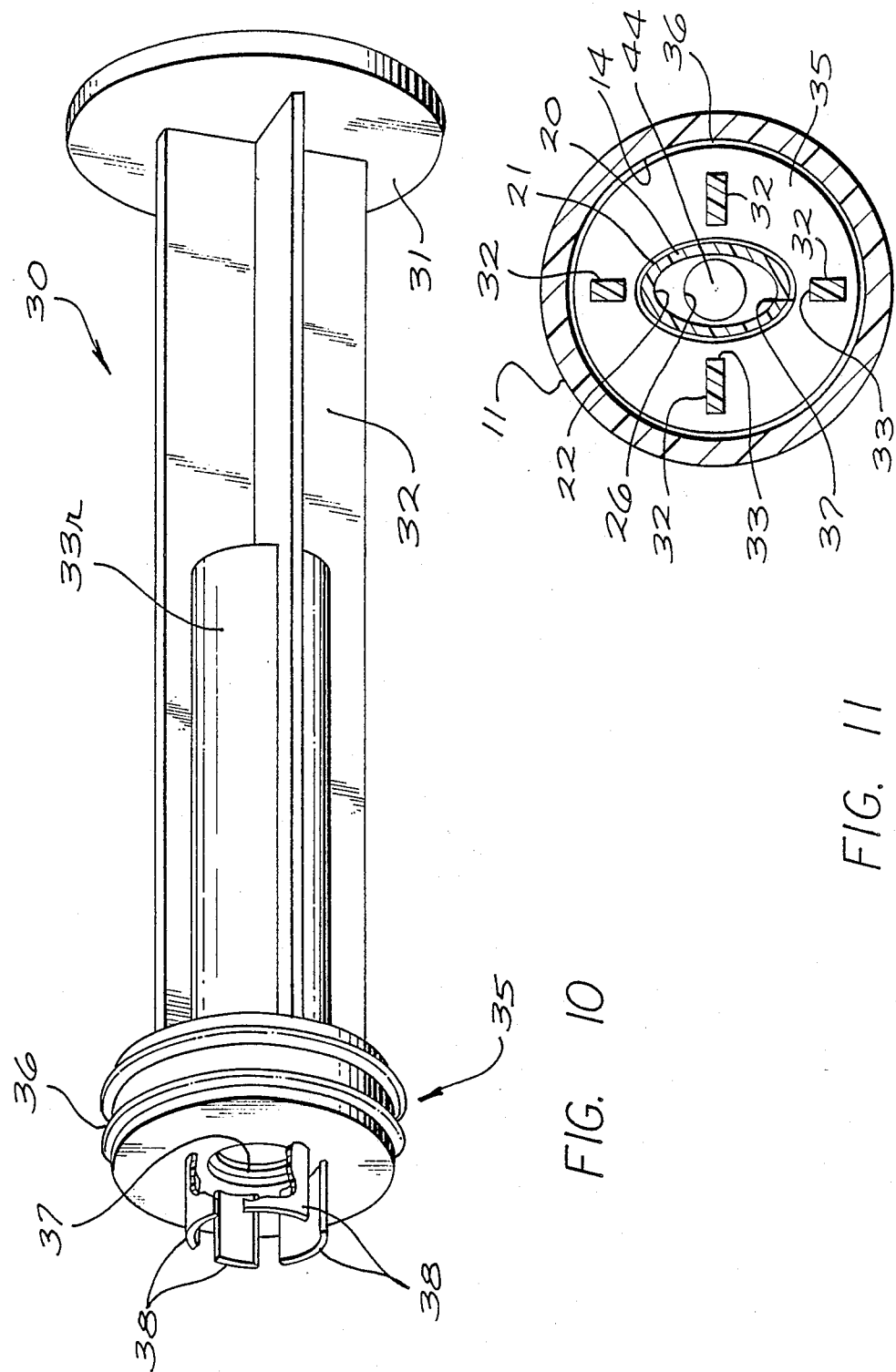
FIG. 10 is a like perspective view of a plunger for use with the FIG. 9 syringe barrel.
FIG. 11 is an elevational view, mostly in cross-section, taken along the line 11—11 in FIG. 1.

The plunger 30 has a generally flat transverse pushbutton 31 at the back end, and a forward-extending shaft consisting of four crossed vanes 32. A cutaway recess or cavity 33 is formed in the front half of the plunger 30, and if desired the plunger can be strengthened as shown in FIG. 10 by providing a reinforcing cylinder 33r within the cutaway recess 33.

Fixed at the front end of the plunger 30 is an elastomeric piston 35. The piston has a formed outer peripheral sealing surface 36 to seat movably against the inner cylindrical surface 14 of the syringe barrel 10, and a formed inner peripheral sealing surface 37 to seat movably against the outer cylindrical surface 21 of the retraction barrel 20.

Also at the front end of the plunger is a segmented, elongated cylinder 38 that projects forward from the piston 35. The diameter of the actuator cylinder 38 is only slightly larger than the outside diameter of the retraction barrel 20—so that the actuator cylinder 38 can extend through the necked-down segment 15 of the syringe barrel 10 and into the narrower nose 16, to engage the retraction mechanism.

The actuator cylinder 38 is segmented (FIG. 10) to clear the retraction-cylinder support vanes 28 within the front end of the syringe barrel 11, 15. To prevent impaction of the actuator-cylinder segments 38 on the support vanes 28, it is necessary to maintain the proper angular alignment between the plunger 30 and the syringe structure 10, 20.

For this purpose, the outside surface 21 of the retraction barrel 20—and the mating inside sealing surface 37 of the piston 35—are advantageously made slightly oval or elliptical (FIG. 11). In other words, both these surfaces are slightly out-of-round, and can be made right elliptical cylinders.

Figure 7:
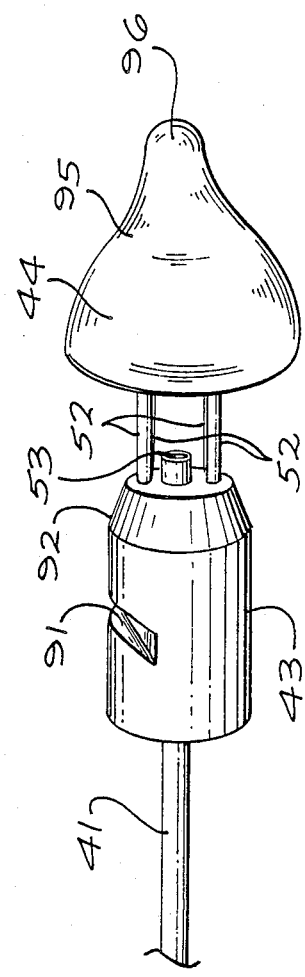
FIG. 7 is a greatly enlarged perspective view, like that of FIGS. 3 and 4, of the needle and carrier structure.
Figure 2:
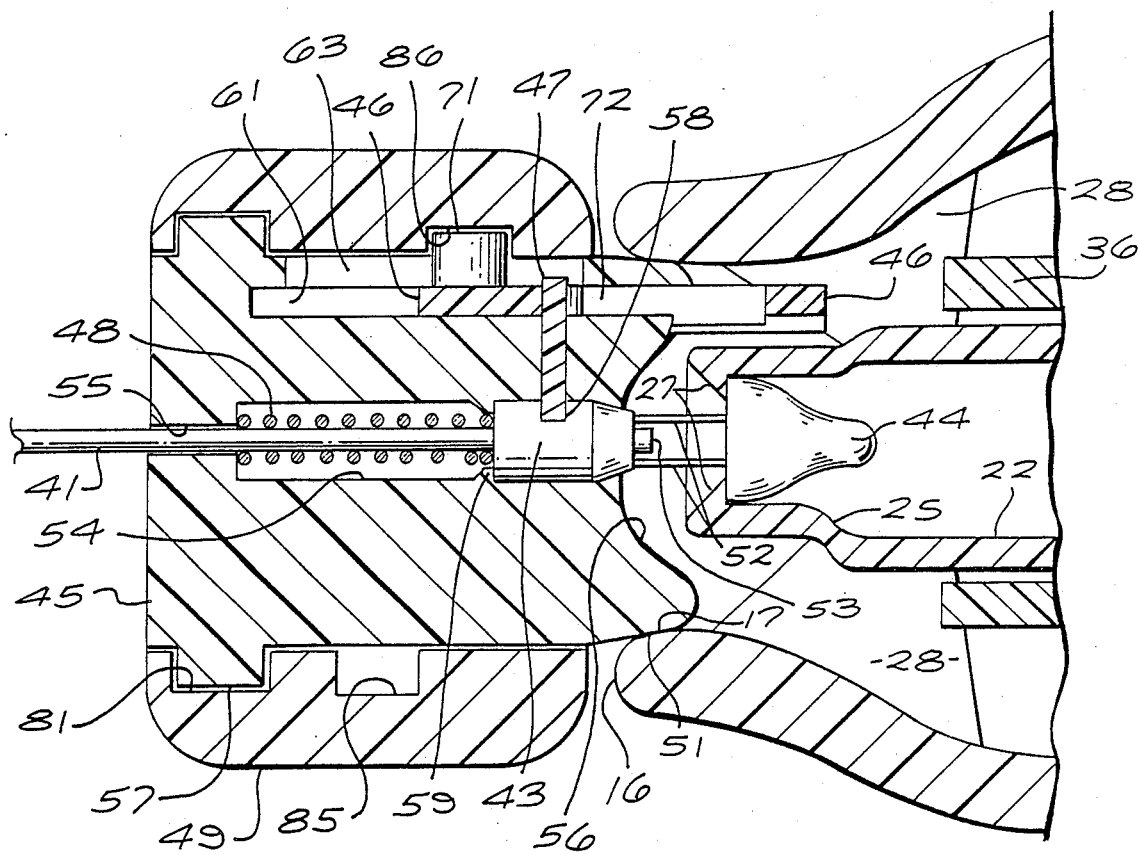
FIG. 2 is an enlarged view of some of the parts of the FIG. 1 embodiment particularly including the needle, hub, and retraction mechanism, in approximately the same condition—namely, before retraction.
Figure 3:
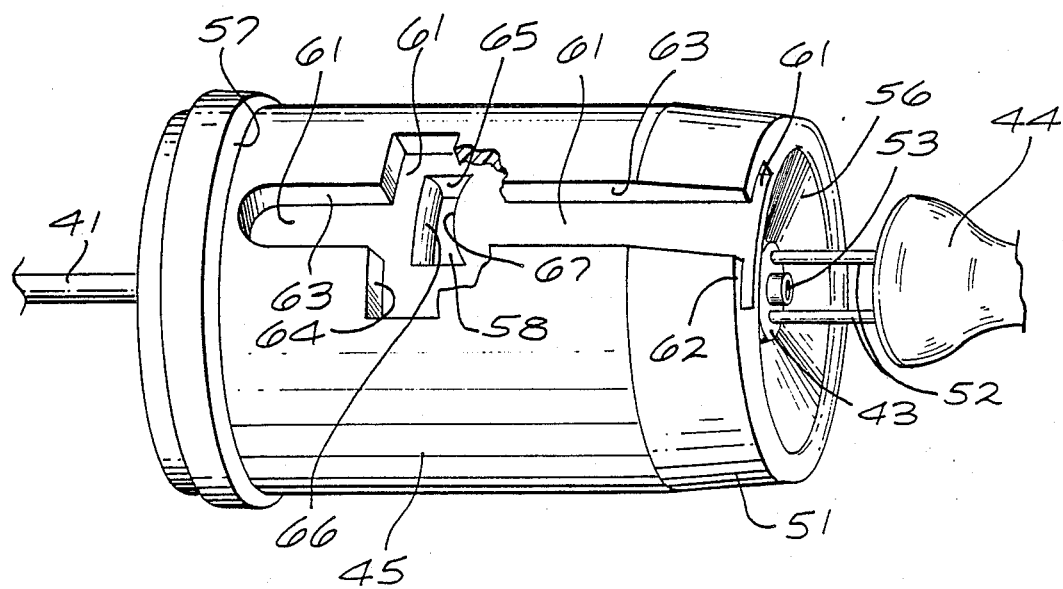
FIG. 3 is an even more greatly enlarged perspective view of the needle, hub and carrier structure that form part of the retraction mechanism of FIGS. 1 and 2.
Figure 8:
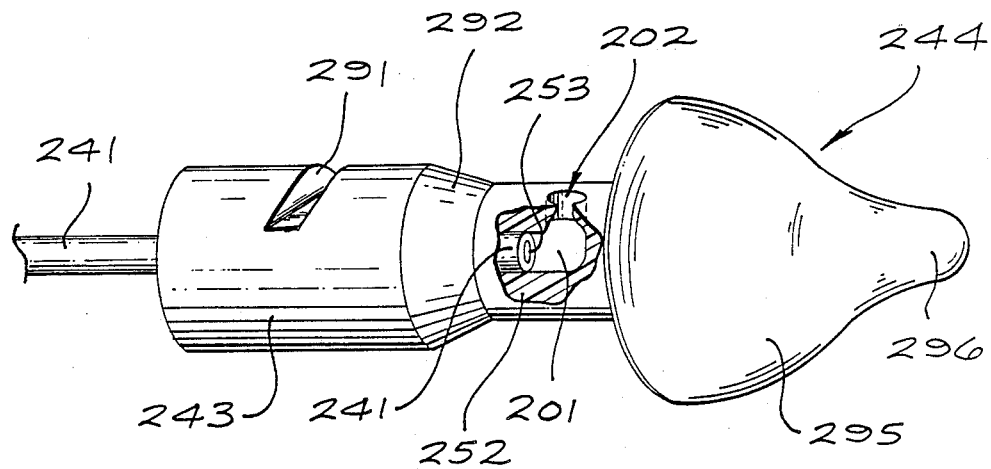
FIG. 8 is a similar view of a variant form of the needle and carrier structure.

The retraction mechanism is housed in a hub 45 (FIGS. 2 and 3), which as previously mentioned has a frustonical inward-tapered rear surface 51 that engages the nose 16 of the syringe barrel 10 in a force fit. Within this hub 45 there is temporarily captured the forward section 43 of a three-part carrier structure 43-52-44 (FIGS. 2, 3 and 7).

The rear end 53 of the needle shank 41 passes through and extends rearward from the forward section 43 of the carrier structure 43-52-44. This forward section 43 is fixed securely and permanently about the needle shank 41.

The front end of the carrier structure seats against an inward-projecting flange 59 within the hub 45. The needle shank 41, however, passes through this flange 59 and through a spring chamber 54, to protrude through a small-diameter aperture 55 at the front of the hub 45.

Within the spring chamber 54, a spring 48 is captured between the front end of the chamber and the front end of the front carrier section 43. Like the shank 41, the rear end of the spring 48 passes through the internal flange in the hub 43.

The spring 48 biases the carrier structure 43-52-44 and needle 41, 42 rearward, but the front carrier section 43 is temporarily held within the hub 45 by a retention tongue 47 (FIG. 2). This tongue 47 passes laterally through a slot 65 (FIG. 3) in the hub 45 and into a forwardly angled lateral slot 91 (FIG. 7) in the side of the front carrier section 43.

A conventional needle-and-hub assembly is generally provided commercially as a separate unit from the mating syringe. These modules are customarily made so that users can fit them together—using either a tapered force-fit assembly, or coarsely threaded connectors of the type currently available commercially by the trade name "Luer".

This modular approach permits various needles of different sizes and types to be combined with any one of various syringes, also of different sizes and types. The embodiments of my invention illustrated here are configured to use this same modular strategy.

Accordingly the rear section 44 of the carrier structure 43-52-44 has a smoothly tapered rear surface 95 ending in a smoothly rounded small tip 96. The tip 96 and tapered surface 95 are made for insertion between the tapered forward surfaces of the teeth 53 at the front end of the retraction barrel 20.

The tip 96 of the rear section 44 is shaped to force the teeth 53 apart very slightly—so that the rear section 44 can seat within the nose 26 of the retraction barrel 20 (FIGS. 1 and 2), against the rear edges of the teeth 53. The interior surface of the retraction-barrel nose 26 seals against the outer periphery of the rear section 44, to deter liquid flow into the retraction barrel 20 during operation of the syringe.

The front section 43 and rear section 44 of the carrier structure are held apart at a generally fixed distance by longitudinal connecting struts 52. This open central structure of the carrier permits free flow of liquid from the annular liquid-containing interior of the syringe 10 into the open rear end 53 of the hollow needle shank 41.

A trigger plate 46 (FIGS. 2 and 4) slides in a longitudinal annular track 61 within one side of the hub 45. At the rear end of the hub 45 this track 61 is accessible for insertion of the trigger plate. Near the forward end of the trigger plate 46 is carried an outward projecting boss 71, for use in arming the retraction mechanism as will be described.

This arming boss 71 extends outward from the trigger-plate track 61 through a longitudinal slot 63 in the outer wall of the hub 45, and projects beyond the outer cylindrical surface of the hub. Hence the trigger plate 46 is free to slide in its track 61, with the arming boss 71 sliding in its slot 63.

A shaped window 65 is cut through the inner wall of the annular track 61, in longitudinal alignment with the previously mentioned retention slot 91 in the side of the front carrier section 43. In the outer wall of the hub, outside the trigger-plate annular track 61, the longitudinal slot 63 is widened in a transverse slot 64 aligned with the inner window 65.

The retention tongue 47 is a separate small plate that extends through the transverse outer slot 64 and inner window 65 in the hub 45, and into the retention slot 91 in the front carrier section 43. The retention tongue 47 also fits through a shaped slot 72-76 in the trigger plate 46, initially at the position illustrated in FIG. 5a.

To clarify this arrangement, I shall describe how the parts are assembled to obtain this condition. First the spring 48 is inserted into its cavity, and then the needle shank 41 is inserted through the spring, cavity and forward aperture 55—and moved forward until the carrier front section 43 is inside the hub and the retention slot 91 is longitudinally aligned just inside the window 65.

The needle shank 41 is held in this position against rearward force of the spring 48, while the plate 46 is installed. The plate 46 is positioned in its annular track 61, toward the front end of the track 61 so that the *rear* end of the shaped slot 72-76 is also longitudinally aligned just outside the window 65 in the hub.

With the needle and trigger plate held so aligned, the retention tongue 47 is inserted through the transverse outer slot 64, the trigger plate 46, and the window 65 into the retention slot 91 in the front section 43. The needle is then released, and the spring forces the carrier rearward so that the angled slot 91 in the front section 43 jams the retention tongue 47 in place.

With these parts of the needle-and-hub assembly 40 so assembled, the trigger plate 46 does not extend rearward out of its annular track. The retraction mechanism is therefore not actuable, except by pushing rearward on the needle shank 41 itself. To prevent this, a generally conventional sheath will be placed over the needle before shipment.

It remains to describe the arming and retraction mechanisms. At the front end of the hub 45 is an outward-extending circumferential boss or flange 57. This flange 57 forms a track for operation of an arming ferrule 49 (FIGS. 1 and 2) that encircles the hub 45.

As diagrammed in FIG. 6, the interior cylindrical surface of the arming ferrule 49 has a continuous circumferential groove 82. It is this groove that engages the flange 57, retaining the ferrule 49 axially on the hub while allowing the ferrule to rotate about the common axis of the ferrule and hub.

As also shown in FIG. 6, another groove 83 is formed in the internal cylindrical surface of the ferrule 49. This latter groove is helical, so that it appears as a longitudinally angled area in the diagrammatic representation of FIG. 6.

When the trigger plate 46 is first installed in its annular track 61 in the hub 45, as previously mentioned the plate 46 is inserted so that the *rear* end of its shaped slot 72–76 is longitudinally aligned with the window 65. In this position the arming boss 71 extends through the *front* end of the longitudinal slot 63 in the outer wall of the hub.

The arming ferrule is accordingly positioned so that the *forward* end 84 of its interior helical groove engages the arming boss 71. The retraction mechanism can be armed later, at any time after (or in principle even before) the hub-and-needle assembly 40 have been fitted to the syringe barrel 10, with the rear section 44 of the carrier structure seated within the retraction barrel 20.

Normally, however, the user will find it more convenient to defer arming the retraction mechanism until just before inserting the needle into the patient—or just after withdrawing it. This choice depends upon the use to which the syringe and needle are being applied.

In particular, when the needle is to be used for injection, it is preferable to delay arming the mechanism until after the syringe has been operated once to fill it with the liquid to be injected. Otherwise the mechanism might be inadvertently actuated when the plunger is fully advanced to begin filling.

Similarly, when the needle is to be used for withdrawal of a sample of liquid from the patient, it will usually be preferable to delay arming the mechanism until after the needle has been taken out of the patient, and just before the needle is inserted into a receptacle that will hold the sample. Otherwise the mechanism might be inadvertently actuated when the plunger is fully advanced to begin taking the sample.

To arm the retraction mechanism, the user rotates the arming ferrule 49 clockwise (as viewed from the user's position), forcing the forward edge of the helical slot 85 against the arming boss 71. The forward edge of the slot drives the arming boss 71, and with it the entire trigger plate 46, rearward in the annular track 61 until the rear end of the plate 46 is fully extended from the rear end of the hub 45, into position for actuation by the actuator boss 36 on the front of the plunger 30.

In the process of driving the trigger plate 46 rearward, the detention tongue 47 passes out of the relatively long, open rear portion 72 of the shaped slot 72–76 in the trigger plate. The tongue 47 is captured instead in a short front section 76 of the shaped slot, in front of two inward projecting trigger teeth 75, as shown in FIG. 5c.

To make the transition to the armed configuration, both the trigger plate 46 and the detention tongue 47 deform as shown in FIG. 5b. As shown in that figure, the gradually tapered cam surfaces 74 at both sides of the slot facilitate rearward and inward curving of the extreme edges of the detention tongue 47, and outward bowing of the lateral edges 73 of the plate. The back edge 67 of the window 65 is curved rearward at its extremes as illustrated, to facilitate curving of the tongue 47.

The tongue 47 thus passes between the trigger teeth 75 at the front end of the cam surfaces 74. It snaps back to a generally planar condition once it is within the front section 76.

At the same time the arming boss 71 passes through a narrowed segment 87 at the rear end of the helical groove 83, and into a broader longitudinal channel 88. A slightly flexible inward projection 87 of the groove wall narrows the groove 83 at its rear end; this projection is shaped as shown to permit escape of the arming boss 71 from the helical groove 83, and to deter reentry of the boss 71 from the longitudinal channel 88 into the helical groove.

Thus the arming boss 71 is rendered free to float longitudinally, with the attached trigger plate 46—except that the retention tongue 47 tends to hold the trigger plate 46 in place longitudinally. The mechanism is now armed.

FIG. 2 shows the arming ferrule and trigger plate just before the mechanism is fully armed, with the arming boss 71 still inside the helical groove 83 but just at its rearmost end 86. FIG. 1 shows the mechanism with the arming boss 71 advanced out of the groove 83 into the longitudinal channel 88. In both drawings the generally central portion 85 of the helical groove is seen at the opposite (lower, as drawn) side of the hub.

After the mechanism is armed, advance of the plunger 30 fully within the syringe barrel 11 brings the actuator boss 36 on the front of the plunger into contact with the rear end of the trigger plate 46, and thereby forces the trigger plate forward.

As the plate moves forward the arming boss 71 slides freely within the longitudinal channel 88 inside the arming ferrule 49. The inward-projecting teeth 75 pull the outer end of the retention tongue 47 forward along the annular trigger-plate track 61.

The outer transverse window 64, in the outer wall of the hub 45, extends slightly forward of the inner window to facilitate this motion. The forward edge of the inner window 65 is rounded forward, to facilitate extraction of the tongue 47 through that window 65. The outer end of the tongue 47 is thus dragged through the inner window as shown in FIG. 12, pulling the inner end of the tongue out of the retention slot 91 in the carrier front section 43.

The carrier structure and needle are thereby freed to fly rearward into the retraction barrel 20, under the influence of the spring 48. This action is facilitated by the outward-tapered forward section 25 of the retraction barrel, which relieves the close fit of the carrier rear section within the barrel immediately as the carrier structure starts back.

As the carrier structure reaches the retaining fingers 97 near the rear of the retraction barrel, the tapered surface 95 of the rear section 44 pushes these retaining fingers 97 apart to allow passage of the carrier. The fingers then spring inward again to capture the front edge of the rear section 44 as FIG. 13 illustrates.

This capture might be seen as superfluous. It may be useful, however, in the event that a user or perhaps other individuals—such as, for example, trash-disposal personnel—might subsequently remove the hub assembly 40 from the front end of the syringe barrel 10, allowing the needle point 42 to project from the opened front end of the syringe.

As shown in FIG. 14 the carrier structure and needle can be started rearward by hydraulic pressure from the liquid in the cylinder, rather than by direct mechanical force. An advantage of this approach is that the liquid performs the necessary reversal of direction, so that the mechanism can be somewhat simpler.

FIG. 14 includes a hub section 145 with inwardly biased detent fingers 146 disposed circumferentially about an internal chamber that holds the front section 143 of the carrier structure. A mating detent ridge 191 is formed about the forward edge of the carrier-structure front section 143.

The detent fingers 146 and detent ridge 191 cooperate to retain the front section 143, once it is in place, against the action of the retraction spring 148. To facilitate initial insertion of the tapered front edge of the front section 143, the rearward faces 174 of the detent fingers 146 are suitably tapered or beveled.

The carrier structure in FIG. 14 does not have the same generally open middle section as that in the embodiment discussed previously. Rather, the central section 152 of this carrier is a continuous slender cylindrical form, terminating in the rear section 144 which is shaped generally as before.

Within the carrier central section is defined a short central longitudinal passageway 101 just behind the open rear end 153 of the needle shank 141. A lateral passage, terminating at its outer end in a a shaped seat 102 for a plug, communicates between the internal longitudinal passageway 101 and the space outside the carrier 143-152-144.

Once the hub 145 is assembled to the syringe, the hollow needle shank 141 is thus in communication with the volume within the syringe. Accordingly forward motion of the plunger (not shown) forces liquid in the syringe outward through the seat 102, passageways 101, and needle shank 141 into a patient.

As in the embodiment previously discussed the carrier rear section 144 is sealed against the forward end of the retraction barrel 122, and the carrier front section 143 is sealed against its peripheral seat 159 within the hub 145. Therefore, as long as the liquid-communication path just described remains open, there is no significant leakage of liquid—either forward, out of the hub through its front orifice 155, or rearward into the retraction barrel.

Within the open rear chamber of the hub, a small plug 102 is suspended by a articulated (or "dogleg") slightly flexible arm 104. The arm 104 is fixed at 105 to the rear interior face of the hub, in such a fashion that the plug 103 is poised just outside the previously mentioned plug seat 102.

Also in the same region is a small actuator cam 106 and actuator rod 107, both suspended by a slightly flexible arm 108. The arm 108 is fixed at 109 to the rear interior face of the hub 145, in position for engagement of the cam 106 with the segmented actuator cylinder 136.

The actuator arm 108 and rod 107 are also shaped and positioned so that when the actuator cylinder 136 engages the cam 106 the rod 107 depresses the plug arm 104. The arm forces the plug 103 toward its seat.

As the plug 103 closely approaches the seat 102, liquid pressure on the rear of the plug 103 tends to force the plug 103 into position firmly, halting liquid flow out through the needle shank 141. Liquid pressure within the syringe then rises sharply, and in particular this higher pressure is applied to the exposed annular forward surface of the carrier rear section 144.

The previously mentioned detent ridge 191 and fingers 146 are dimensioned, in relation to the resilience of the material of both parts, to satisfy two conditions.

First, liquid pressures normally applied to the carrier rear section 144 in operation of the syringe to expel liquid through the needle are too small to separate the detent elements.

Second, liquid pressure applied by continued operation of the syringe after the plug 102 is seated are large enough to separate the detent elements. As the carrier starts backward, the dogleg or articulation of the plug arm 104 extends slightly so that the plug 103 can follow its seat 102 backward momentarily.

At the same time the inwardly projecting teeth or hooks at the front of the retraction barrel 122 tend to deform slightly to follow the carrier rear section 144 backward. This action helps to momentarily maintain a liquid seal around the rear section, while the detent fingers 146 partially hold the seal around the front edge of the forward section 143.

This brief maintenance of the liquid seals sustains the rearward pressure on the carrier rear section 144 long enough to fully withdraw the detent ridge 191 on the carrier front section 143 from the detent fingers 146 inside the hub 145. The carrier structure and needle are then propelled rearward by the coiled spring 148, safely retracting the needle into the inner barrel 122 as previously described. In the process the plug arm 104 bends radially outward enough to permit the carrier to escape the plug.

FIGS. 15 and 16 illustrate an embodiment that is simpler and easier to construct. Because it departs from the customary "in line" exterior configuration of previous syringes, however, it may be less appealing commercially.

In this embodiment the retraction barrel is mounted outside the syringe barrel, in a side-by-side configuration as shown. The needle is mounted in the front end of the retraction barrel.

Hence the needle axis is offset from that of the syringe plunger, producing a noticeably different "feel" in operation of the unit. Objectively, however, this device offers several benefits.

A conventional plunger shank (e. g., crossed vanes) can be used. The shank can be tipped with a solid (rather than annular) syringe piston. The syringe and retraction sections can be made in a unitary form as suggested by FIG. 15, or as two separate modules as shown in FIG. 16 for greater convenience in combining various syringe sizes and types with various needle sizes and types.

In either case a lateral passage 401 between the forward end of the syringe section 410 and the retraction-barrel section 420 carries liquid from the syringe to the carrier 443. The carrier advantageously has a hollow interior, defining axial and radial passages 403 from the exposed rear opening of the hollow needle 441 to the exterior side wall of the carrier (as in the previously discussed hydraulic-trigger embodiment of FIG. 14).

The lateral passage 401 in the wall of the retraction barrel 420 is extended in a circumferential channel 404 that encircles the carrier 443, in axial alignment with the lateral passage 403 in the carrier. This channel 401 allows liquid from the syringe to reach the hollow needle shank 441 regardless of the angular orientation of the lateral passage 401 about the axis of the carrier If the syringe and retraction barrel are separate modules as in FIG. 16, the outlet from the front of the syringe is advantageously shaped into a sealing nozzle 401. This nozzle very closely fits into a mating recess at the outer end of the passage 401 in the retraction barrel.

The mutually facing surfaces of the two modules are made to mate—as, for example, both planar as suggested in FIG. 16—with a detent appendage 429 and socket 428 respectively spaced from the nozzle 401 and recess so that the two modules readily snap together at two points. Finger grip channels 405 may be provided if desired.

A retraction trigger for the embodiment of FIG. 15 or 16 may be selected from a variety of forms. The strategy of either the FIG. 1 or FIG. 14 embodiment can be employed, with straightforward adaptations that will now be clear to those skilled in mechanical design, to cause retraction in response to operation of the plunger 330 or 430.

My preference for use in the FIG. 15 or 16 embodiment, however, is a simple mechanical trigger with a separate manual actuator. A suitable trigger for this purpose, usable without significant modification, is illustrated in FIGS. 1 through 3a of my previously mentioned copending patent application.

All of the embodiments discussed so far employ biasing means such as a spring to propel the needle and carrier rearward into a stationary retraction barrel. Neither the spring nor a stationary receptacle is necessary, however, as shown in FIG. 17 and 18.

Here the carrier front section 543 has internal passageways terminating at its external side wall in an orifice 501, to carry liquid from the syringe into the hollow needle shank 541. In the vicinity of the orifice 501 the carrier is tapered inward toward the rear, forming a detent surface.

Inward-biased detent fingers 502 are formed inside the hub 545 to engage the tapered surface of the carrier side wall. The rear section of the carrier is formed as a rearward-facing barb 544, with a sharply pointed tip 596 tapering at intermediate surfaces 595 to slightly flexible trailing edges 594.

The front end of the plunger 530 is enclosed to form a movable retraction barrel 521, 522 that is carried on the plunger itself. The front end of this barrel has a molded mosaic-like face consisting of several isosceles trapezoidal sections 527, their broad bases along the periphery of the face and their narrower vertices arrayed about the center, and all angled rearward toward the center of the pattern.

The individual trapezoidal sections are separated along the isosceles sides by narrow weakened strips 593 to facilitate breaking of the front face of the barrel into several separate petal-like segments—under circumstances to be described shortly. The peripheral bases of all the trapezoidal sections are also fixed to the peripheral wall of the inner barrel by narrow weakened strips 598, to facilitate rearward hinging of the individual petals after breakage.

At the center of the mosaic pattern is a generally circular aperture, which is hermetically sealed by a frangible seal 597. In operation of the syringe to dispense liquid, the mosaic face elements 527-593-598 and the frangible seal 597 all function as a part of the liquid-impelling face of the piston 535.

At the end of the piston stroke, however, the frangible seal 597 is impaled on the barb 544, and the tip 596 of the barb enters the retraction barrel or chamber 522. As the piston advance further the tapered edge 595 forces the "petals" or segments 598 of the front face of the barrel 522 apart slightly, breaking the weakened sections 593 and forcing the segments to hinge rearward slightly about their peripheral bases 598.

When the trailing edges 594 of the barb enter the chamber 522 through the broken seal 597 and rearward-hinged segments 527, the latter spring forward and inward slightly. After this has occurred, the user of the syringe reverses direction of the plunger, pulling the mosaic segments back against the trailing edges 594 of the barb.

This force draws the carrier out of the detent fingers 502 and pulls the carrier and needle into the syringe body. When the needle passes the detent fingers 502 in the hub 545, these fingers snap together, blocking reinsertion of the needle through the hub.

The syringe may now be discarded, as the needle is safely contained within it. If preferred to minimize the bulk of the item to be discarded, the plunger handle may now be advanced once again: the point 542 of the needle will be trapped in a peripheral groove surrounding the detent fingers 502 in the rear of the hub, preventing forward motion of the needle while the retraction barrel is advanced forward around the needle.

If medical personnel do not choose to advance the plunger at that time, and if disposal personnel later inadvertently advance the plunger in the course of preparing to discard the assembly, as will now be evident the result will be just the same as if medical personnel had deliberately done so. That is, the needle will remain within the unit while the retraction barrel moves forward around it.

If desired, a ratchet-like lock (not shown) can be provided to prevent withdrawing the plunger once it is advanced fully home with the needle in it. This feature may not be preferred by some users, since premature operation of the lock could prevent retraction of the needle.

Figure 19:
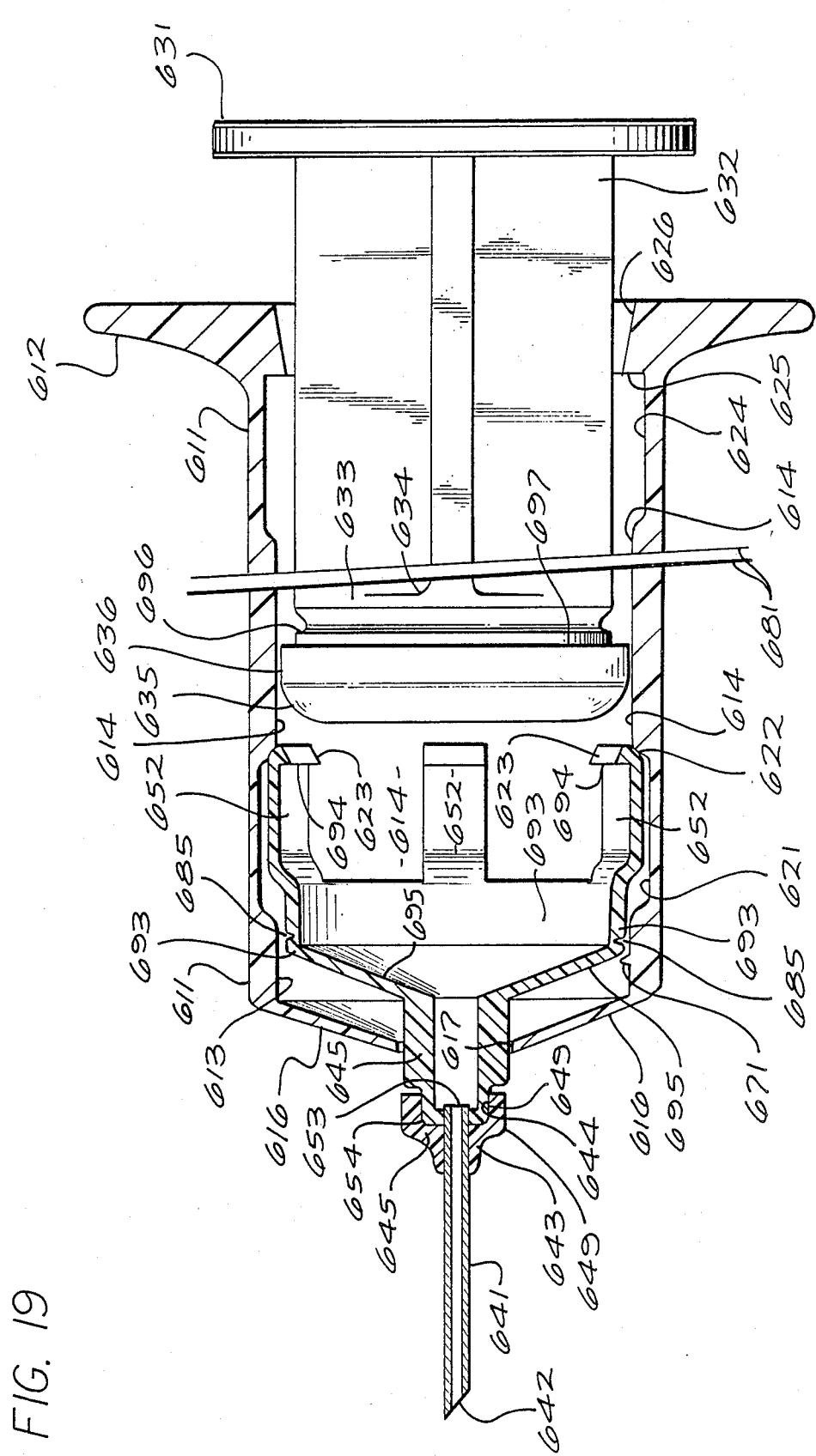
FIG. 19 is an elevation, mostly in longitudinal section, of a fifth embodiment. In this embodiment the plunger shaft is pulled back to retract the needle, and then pulled entirely out of the barrel for disposal. Most of the length of the device is omitted from this view.

Another embodiment of my invention—also requiring neither a spring nor a separate receptacle for the needle after retraction—appears in FIG. 19. This form of the invention is particularly advantageous in that it can be used with an entirely standard needle 641 that carries a standard hub 643 sized and configured for attachment to other types of syringes available on the market.

Such a standard hub 643 may for example be of the type known commercially by the trade name "Luer" and may be either a friction-fit or twist-lock variety. Of course many other mounting arrangements, either in commercial use or conceivable, are suitable for use with the present invention.

Regardless of the particular attachment configuration used, however, the embodiment of FIG. 19 is beneficial in that it can take advantage of the great variety of needle lengths, prices, and other variables that are already provided or may come to be provided on the open market. This benefit may be of value to a medical facility that has a large stock of needles, or wishes to continue purchasing particular needle types in large quantity, for various other purposes not calling for a safety device. Such a facility can continue with those commercial purchasing practices, and will not be required to obtain and stock an entirely new needle type for use with my invention.

I wish to emphasize, and it will be clear to people skilled in the field of syringe and needle design, that most or all of the other forms of my invention described and discussed hereinabove are also amenable to redesign or reconfiguration for use with commercial-standard needles. The embodiment of FIG. 19 is, however, especially suited to use of such needles in a particularly straightforward and economic fashion.

I also wish to emphasize that, although the embodiment of FIG. 19 is particularly advantageous in its suitability to use with standard needles, it need not be limited to such use. This embodiment is also equally usable with *non*standard or custom needles—or even needles permanently and integrally fixed to the rest of the syringe device—for whatever commercial or economic reasons that may be desired.

The FIG. 19 embodiment includes a syringe barrel 611 that has an elongated interior with a substantially cylindrical lengthwise interior wall 621, 622, 614, 624, 625, 626, terminating at its forward end in a transverse forward end wall 616. Although substantially cylindrical, the interior wall of the barrel is not a simple cylinder, rather having various important surface details to be discussed below.

The barrel also defines in its tranverse forward end wall 616 an aperture 617 that is large enough to pass the standard hub 643—or other attachment adaptation which the needle may have. The aperture 617 is too small, however, to pass a finger of an adult person of normal size.

The embodiment of FIG. 19 also includes a sealing plate 695, slidably disposed within the barrel 611 near the transverse forward end wall 616. The sealing plate 695 seals against the interior of the barrel.

In the particular configuration shown in FIG. 19, the sealing plate 695 has a rearward extending cylindrical skirt 693, and it is this skirt that seals against the interior of the barrel—more specifically, against the cylindrical interior wall 613 just rearward of the transverse end wall 616. It should be appreciated, however, that alternative configurations are readily provided in which the sealing plate seals instead, e. g., against the forward transverse end wall 616 or even against the interior of the aperture 617. (Such alternative forms may require a different arming mechanism that allows the sealing plate 695 to be fully forward during use of the syringe.)

The FIG. 19 embodiment also includes a forward-extending hub attachment 645, carried on the sealing plate 695 and aligned with the aperture 617 in the transverse forward end wall 616. This forward-extending attachment 645 is provided for attaching the standard hub or other attachment adaptation 643 of the needle 641 to the syringe barrel 611.

It will be understood that this attaching of the hub or other adaptation 643 "to the syringe barrel 611" is indirect, through the intermediary of the sealing plate 695 and its forward-extending attachment 645. The needle 641 is thus attached with its sharpened shaft end 642 of the needle projecting forward from the syringe barrel.

The forward-extending attachment 645 has a small central orifice for passage of liquid between the hollow needle shaft 641 and the interior of the syringe barrel. Once again, the invention may be implemented in a configuration that includes the needle 641 as an integrally attached element—in which case the attachment extension 645 and the needle hub 643 may in effect be a single unitary part.

The FIG. 19 embodiment also must have some means for securing the sealing plate 695 and forward-extending attachment 645 against rearward motion out of the syringe. In the embodiment shown here, the action of these securing means is very light, because as will be seen a separate arming feature is provided to deter premature retraction.

Accordingly the securing means consist essentially of (1) the frictional fit between the cylindrical skirt 693 of sealing plate 695 and the cylindrical interior wall 613 in the forward portion of the barrel 611, augmented by (2) the added slight resistance provided by engagement of several radially inward-extending hooks 695 with a radially inward-sloping cam surface 622.

This cam surface 622 is annular and forms the rearward termination of an annular groove 621 in the cylindrical wall 613, 614; the principal purpose of these annular features will be described below. For forms of this invention in which no arming mechanism is provided—or in which the sealing plate 695 seals against, for example, the transverse end wall 616—more forcible securing means may be required.

The illustrated embodiment also includes a syringe plunger 631–636, 696, 697, which is disposed at least partially within the syringe barrel 611. This plunger is adapted to be moved forward while maintaining a seal within the syringe barrel, to drive liquid out of the barrel and through the hollow needle shaft 641 into a patient. To adapt it for these functions, the plunger is fitted with a piston 635 that has a resilient peripheral surface 636. This surface of course seals slidably against the interior cylindrical surface 614 of the barrel.

The plunger also includes a handle 631 and a shaft 632, 633, 634, for actuating the piston 635, 636 as described above. FIG. 19 has been drawn with most of the length of the syringe barrel 611 and plunger shaft 632, 633 omitted, to permit illustration of the detailed parts at a relatively high enlargement. It will be noted, however, that at some point along the shaft there is a transition structure 634 between two distinct portions of the shaft.

Specifically, these are a relatively more economical shaft structure, e. g. a cruciform shape 632, and a more solid shape 633 that is suited for certain functions to be described below. The transition structure 634 may be near the piston portion 635, 636 of the plunger as suggested in FIG. 19, or may be further rearward as preferred.

This embodiment further includes some means for releasing the securing means and retracting the sealing plate 695. These releasing and retracting means do not retract only the plate 695 alone, but with it the forward-extending attachment 645, and also retract the needle 641 and its hub or other attachment adaptation 643. These parts are retracted in their entirety into the syringe barrel and beyond reach of an adult person's fingers.

The releasing and retracting means are mutually engaging. By this phrase I intend to specify that the releasing and retracting means are dual means having two groups of parts, and that these two groups of parts mutually engage each other.

More specifically, certain portions of the releasing and retracting means are located on a forward end of the plunger 631–636, and other portions are located on a rearward side of the sealing plate 616 or attachment 645. These respective parts mutually engage each other.

The portions located on the plunger 631–636 particularly include a shaped circumferential groove 696 encircling the forward cylindrical portion 633 of the plunger shaft 632–634. The portions located on the rearward side of the sealing plate 616 here include the hooks 652 mentioned earlier.

As shown in FIG. 19 the device is armed for retraction. In this condition the rearward ends or tips 694 of all the hooks 652 are driven partway up the previously mentioned annular cam surface 622. (These hooks are biased radially outward, so that when not cammed inward they tend to move toward the furthest radially outward position permitted.)

In this position the hook tips 694 project slightly further radially toward the center of the barrel than if they were not riding up the cam surface 622. The tips terminate, however, in bevels 623 that are shaped to permit forward passage of the piston 635 and particularly its resilient periphery 636.

Now when the plunger 631-636, 696, 697 is driven fully forward, the piston 635 passes the beveled tips 623 of the hooks 652. In this way, although the piston periphery 636 may not seal perfectly at the slightly irregular surfaces between the hooks 652, the piston 635 expels most of the liquid in the forward portion of the barrel 611 out through the hollow needle shaft 641.

Next the user can withdraw the plunger rearward. At the very beginning of this return stroke, there is slight axial motion of the piston 635, 636 relative to the skirt 693 and hooks 652. This short motion will suffice to suck any liquid in the hollow needle shaft 641 rearward from the tip 642 toward the interior of the syringe—and possibly entirely into the interior of the syringe—to minimize leakage of liquid that may be contaminated.

As the return stroke proceeds, the forward corners of the tips 694 catch in the complementarily shaped annular groove 696 in the forward portion 633 of the plunger shaft. The tips 694 and the other parts of the hooks 652 are thereby pulled rearward with the plunger.

As will now be clear, the skirt 693 and sealing plate 695, with the forward extension 645 and needle 641 attached, similarly move rearward toward the open rear end 626 of the barrel 611. Once this motion begins, the hooks ride fully past the annular cam surface 622 onto the smaller-diameter portion 614 of the syringe barrel proper.

In this radially inward position, the hooks even more securely engage the annular groove 696 in the plunger shaft forward portion 633, so that the sealing plate 696 and needle 641 are firmly retracted into the barrel 611. When the plunger is moved rearward by the length of the needle plus the attachments 643, 644, 645, the needle tip 642 is retracted through the aperture 617 in the transverse front wall 616.

Still further rearward motion of the plunger handle 631 retracts the needle tip 642 safely well inside the aperture 617, beyond reach of the fingers of the user or any other person whose hands are of normal adult size. If desired the design safety margin can be increased by providing slight additional retraction distance so that contact with even the fingers of determined small children can be made distinctly difficult or impossible—although access by such children to discarded syringes would be extraordinary.

At the rear end of the barrel 611 another annular groove 624 is formed, somewhat analogous to the forward groove 621 previously mentioned. The rear groove 624, however, terminates in a positive stop surface 625 that may be at a right angle to the syringe axis, or even angled forward (toward the centerline of the barrel).

This stop surface 625 is formed as an inner flange within the rear end of the barrel 611. It positively and firmly halts the rearward surfaces of the hooks 694, and thereby the rearward motion of the hooks, skirt 693, sealing plate 695, attachments 643-645, and needle 641.

As the hooks 652 are biased radially outward into the annular groove 624, however, the sharp forward corners of the tips 694 retreat radially out of the annular groove 696 in the plunger shaft 633—allowing the plunger shaft 631-634 to proceed rearward past the flange 625 and out of the barrel.

The rear annular groove 624 is made shallower than the forward groove 621, so that the hook tips 694 while extracted from the annular groove 696 do not clear the rear peripheral edge of the piston 635, 636. The piston is advantageously constructed as a separate section from the plunger shaft 632-634, so that when the hook tips 694 stop the rearward motion of the piston 635, 636 the piston separates from the shaft.

In this way the shaft 631-634 is removed entirely from the barrel 611, leaving the piston 635, 636 trapped within. As previously mentioned this arrangement may be important if the syringe is used for drawing blood, so that significant quantities of contaminated liquid may be present within the syringe.

The forward end of the assembly can be made to remain sealed by the sealing plate 695 and skirt 693, if desired. Alternatively the device can be configured to relax the seal after retraction so that the needle does not remain pointed toward the center of the aperture 617.

The flange 625 can be contoured along its radially inner face 626 to provide a frustoconical ramp or cam that is widest at its rearward outer end. This contour facilitates initial insertion of the piston 635, 636.

It will be recalled that FIG. 19 illustrates the invention in its armed condition, ready for retraction. Generally, however, a user will wish to fill the syringe before a final expulsion stroke. In that step, for the following reason, the user will not want the device to be armed.

A syringe usually is filled, e. g., either with medication, preparatory to expelling the medication into a patient; or with a blood sample from the patient, preparatory to expelling the sample into a receiving container. In either event the user will want to advance the plunger fully forward just before beginning to fill the syringe—but will want to avoid triggering retraction in the process.

The device of FIG. 19 includes an arming feature for the user's assistance in avoiding premature retraction. Specifically, formed in the outer peripheral surface of the skirt 693 is a coarse circumferential spiral groove 685. Formed in the interior cylindrical surface 613 of the barrel 611, just rearward of the transverse end wall 616, is a radially inward-projecting tooth 671 adapted to ride in the spiral groove 685.

When the device is assembled, the sealing plate 695 is inserted into the barrel and moved to its forward position as shown in FIG. 19, with the forward extension 645 protruding partway through the aperture 617. The plate 695 and attached parts are then rotated to thread the tooth 671 along the spiral groove 685.

This rotation draws the sealing plate 695 and extension 645 forward toward or against the inner surface of the transverse end wall 616. In that position (not illustrated) the teeth 652 are moved forward so that their tips 694 are not riding up on the annular cam surface 622 but rather are permitted to move outwardly, as biased, into the annular groove 621.

When so positioned the hook tips 694 radially clear the annular groove 696 in the plunger shaft forward portion 633—and furthermore clear the mating portions at the rear of the piston 635, 636. Accordingly the piston can be advanced fully forward and then rearward to fill the syringe, without actuating the retraction mechanism.

As indicated in my previously mentioned copending application, the syringe and retraction barrels in the various embodiments of my invention are preferably but not necessarily injection molded from plastic such as polycarbonate. Like material is suitable for the plungers.

Similarly the hubs and carrier structures—including various articulated appendages such as the plug and cam arms 104, 108 in FIG. 14—may be cast as unitary forms in the plastic available commercially available under the trade name "Delrin". Alternatively if preferable some appendages may be secured in place as by sonic welding, cement or other means.

The needles are generally conventional, and made of stainless steel. Other metal parts, such as coil springs, where needed are also advantageously of stainless steel.

A very generally conventional safety cover (such as that shown in FIG. 16 of my copending previous application) should be provided for the needle of my invention. Such a cover protects against accidental puncture and against contamination of the needle before use.

The cover must be adapted to fit over the arming ferrule of FIG. 1, trigger pushbutton 42 disclosed in my previously mentioned copending application, or any other functioning elements that may be incorporated into practical designs. The cover should be designed so that it does not trigger such elements.

It is preferable also for such safety covers to fit against the operative or moving elements—or between the operative elements and the adjacent stationary parts—to block movement of the movable elements due to vibration in shipment or other handling. For these purposes of desirable safety-cover mounting, as will now be clear, minor modifications of the configurations herein illustrated may be required.

After use the safety cover may be thrown away. In particular, it may be discarded either together with my invention or separately, since the needle is automatically sheathed without the cover.

I consider the embodiments described above highly desirable. Various features, however, could in principle be omitted and the device still correspond to my invention as most broadly envisioned and claimed.

For example, in the spring-powered forms of the invention, a tension spring (rather than a compression spring as shown) could be secured to a small hole or hook near the rear end of the needle, to pull the needle rearward without the intermediary of a carrier structure. Alternatively the spring could be omitted, and the needle arranged to fall into the handle under the influence of gravity when released.

Moreover it is not necessary that the rear end of the needle initially be within the syringe or retraction barrel. Some other element of the apparatus could instead pull the rear end of the needle rearward.

On the other hand, it is not entirely necessary that after actuation of the latch the rear end of the needle come to rest within the retraction barrel: in principle the "back" of the needle could protrude from the rear end of the barrel. In this case proper provision must be made, however, to prevent the needle from being accidentally reextended forward—and also to prevent personal contact with residual liquid that may leak from the rear end of the needle, if such liquid may be contaminated.

By virtue of the arming arrangements and the syringe-plunger-actuated retraction arrangements described above, accidental premature operation of the retraction mechanisms in the various embodiments of my invention are unlikely. Even in event of such an accident, there is no harm to the patient or medical personnel.

The main adverse result of such an accident if it does occur is economic: another syringe must be obtained. It is my expectation that regular users of the device will quickly learn to avoid inadvertent triggering of the latch.

Various features or elements that have not been specifically identified above appear in some of the drawings herein. In most instances those features or elements are substantially identical to the items in FIGS. 1 through 13 that have corresponding reference numerals—i.e., numerals that differ only by addition of a prefix "1" through "5" in FIGS. 14 through 18.

As in the cannula-insertion set described in my above-mentioned copending application, some movable latch elements may be mounted to the syringe-and-retraction-barrel portions of the apparatus or to the hub portion, mutatis mutandis. Similarly, to control the overall length of the device it is desirable to exercise careful design to minimize the distance from the front of the hub to the rear of the needle.

It will be understood that the foregoing disclosure is intended to be merely exemplary, and not to limit the scope of the invention—which is to be determined by reference to the appended claims.

I claim:

1. A safety device for use in injecting liquid into or withdrawing liquid from a patient and for thereafter protecting people from contact with portions of the device that have been within the patient; said device comprising:
    a hollow needle for piercing such patient and for guiding and carrying such liquid into or out of the patient, said needle having a hollow shaft with at least one sharp end;
    a syringe that includes:
        a syringe barrel for containing a quantity of such liquid, and
        a syringe plunger disposed at least partially within the syringe barrel and adapted to be moved forward within the syringe barrel to drive such liquid out of the syringe barrel and through the hollow shaft into such patient;
    means for securing the needle shaft to the syringe barrel, with the sharp end projecting from the syringe barrel; and
    manually actuable means for releasing the securing means and for substantially permanently retracting the sharp end of the needle into the syringe and beyond reach of such people's fingers;
    wherein the plunger is relieved to permit retraction of the sharp end of the needle by the releasing and retracting means into a space within the syringe, while the plunger is disposed forward within the syringe barrel; and
    wherein the releasing and retracting means are manually actuable by a simple unitary motion, of amplitude that is substantially shorter than the shaft of the needle.

2. The device of claim 1, wherein:
    the plunger is relieved by formation of a hollow within the plunger.

3. The device of claim 1, wherein the syringe barrel comprises inner and outer walls defining:
- an annular volume, between the inner and outer walls, for containing such liquid; and
- an inner volume, within the inner wall, for receiving at least part of the needle and at least part of the securing means.

4. The device of claim 3, wherein:
- the plunger has an annular piston disposed within the annular volume and movably sealed against both walls; and
- the plunger defines a hollow that penetrates the piston and receives the inner wall of the syringe barrel;
- whereby said at least part of the needle and at least part of the securing means when received in the inner volume of the syringe barrel are effectively within the hollow in the plunger.

5. The device of claim 4, further comprising:
- sealing means for substantially preventing flow of such liquid into the inner volume before manual actuation of the releasing and retracting means.

6. The device of claim 5, further comprising:
- a carrier structure fixed to and extending from the needle, and adapted to be restrained within the device with the sharp end of the needle projecting from the syringe; and adapted for motion within the device, responsive to the releasing and retracting means, to withdraw the needle into the syringe; and
- means cooperating with the carrier structure to define a substantially annular void associated with the syringe barrel, forward of the carrier structure, encircling the needle shaft; and
- wherein the releasing and retracting means comprise a spring disposed in compression within the void, for propelling the carrier structure and needle rearward; and
- further comprising sealing means for substantially preventing flow of such liquid into the substantially annular void.

7. The device of claim 6, wherein the carrier structure is elongated in the forward-to-rearward direction and comprises:
- a rear circumferential seal that forms said inner-volume sealing means;
- a front circumferential seal that forms said annular-void sealing means; and
- a lateral passageway within the carrier structure and communicating with the hollow shaft, for admitting such liquid from the syringe barrel into the hollow shaft.

8. The device of claim 4, wherein:
- the releasing and retracting means are actuated by mechanical pressure from the syringe plunger.

9. The device of claim 4, wherein:
- the releasing and retracting means are actuated by hydraulic pressure from such liquid, pressurized by manipulation of the syringe plunger.

10. The device of claim 4, wherein:
- the releasing and retracting means comprise a spring disposed and attached to propel the sharp end of the needle into the syringe when the releasing and retracting means are manually actuated.

11. The device of claim 4, further comprising:
- means for preventing escape of the sharp end of the needle from the syringe after actuation of the releasing and retracting means.

12. The device of claim 1, wherein:
- the releasing and retracting means are manually actuable by manipulation of the syringe plunger.

13. The device of claim 1, wherein:
- the releasing and retracting means are actuated by mechanical pressure from the syringe plunger.

14. The device of claim 1, wherein:
- the releasing and retracting means are actuated by hydraulic pressure from such liquid, pressurized by manipulation of the syringe plunger.

15. The device of claim 1, further comprising:
- means for preventing escape of the sharp end of the needle from the syringe after actuation of the releasing and retracting means.

16. The device of claim 1, wherein:
- the releasing and retracting means comprise a spring disposed and attached to propel the sharp end of the needle into the syringe when the releasing and retracting means are manually actuated.

17. The device of claim 16, wherein:
- the releasing and retracting means are manually actuable by manipulation of the syringe plunger, starting generally at a forward end of its forward motion within the syringe barrel, to release the needle for rearward propulsion by the spring.

18. The device of claim 17, wherein:
- the releasing and retracting means are actuated by mechanical pressure from the syringe plunger, generally at the forward end of its forward motion, to release the needle for rearward propulsion by the spring.

19. The device of claim 17, wherein:
- the releasing and retracting means are actuated by hydraulic pressure from such liquid, pressurized by forward motion of the syringe plunger, generally at the forward end of its forward motion, to release the needle for rearward propulsion by the spring.

20. A safety device for use in injecting liquid into or withdrawing liquid from a patient and for thereafter protecting people from contact with portions of the device that have been within the patient; said device comprising:
- a hollow needle for piercing such patient and for guiding and carrying such liquid into or out of the patient, said needle having a hollow shaft with at least one sharp end;
- a syringe that includes:
  - a syringe barrel for containing a quantity of such liquid, and
  - a syringe plunger disposed at least partially within the syringe barrel and adapted to be moved forward within the syringe barrel to drive such liquid out of the syringe barrel and through the hollow shaft into such patient;
- means for securing the needle shaft to the syringe barrel, with the sharp end projecting from the syringe barrel; and
- manually actuable means for releasing the securing means and for substantially permanently retracting the sharp end of the needle into the syringe and beyond reach of such people's fingers;
- wherein the plunger is relieved to permit retraction of the sharp end of the needle by the releasing and retracting means into a space within the syringe, while the plunger is disposed forward within the syringe barrel.

21. The device of claim 20, wherein:

the plunger is relieved to permit retention of the retracted needle within the syringe while the plunger is subsequently again moved forward within the syringe barrel.

22. The device of claim 21, wherein the plunger is relieved by formation of a cavity therein to receive the retracted needle; and further comprising:
- a frangible seal disposed over a mouth of the cavity to substantially prevent entry of such fluid into the cavity, generally before actuation of the releasing and retracting means; and
- seal-rupturing means carried with the carrier structure for rupturing the sealing means, generally at the time of actuation of the releasing and retracting means.

23. The device of claim 20, wherein:
- the releasing and retracting means comprise mutually engaging means on a forward end of the plunger, and on a rearward end of the securing means or needle;
- whereby the needle is rearwardly retracted into the syringe by rearward manipulation of the plunger.

24. The device of claim 23, wherein:
- the seal-rupturing means and mutually engaging means are both provided, in common, in the form of a rearward-facing barb carried on a rearward face of the carrier structure.

25. The device of claim 23, wherein:
- the seal-rupturing means and mutually engaging means are both provided, in common, in the form of a rearward-facing barb carried on a rearward end of the needle; and
- the needle defines a lateral passageway forward of the barb for flow of such liquid from the syringe barrel into the hollow shaft.

26. The device of claim 23, further comprising:
- ratchet means for restraining the needle against forward motion after the carrier structure is drawn rearward into the syringe barrel.

* * * * *